US006383273B1

(12) United States Patent
Kepner et al.

(10) Patent No.: US 6,383,273 B1
(45) Date of Patent: May 7, 2002

(54) COMPOSITIONS CONTAINING A BIOCIDAL COMPOUND OR AN ADSORBENT AND/OR CATALYST COMPOUND AND METHODS OF MAKING AND USING THEREFOR

(75) Inventors: Bryan E. Kepner, Atlanta; Eric A. Mintz, Roswell, both of GA (US)

(73) Assignee: Apyron Technologies, Incorporated, Atlanta, GA (US)

( * ) Notice: Subject to any disclaimer, the term of this patent is extended or adjusted under 35 U.S.C. 154(b) by 0 days.

(21) Appl. No.: 09/373,486

(22) Filed: Aug. 12, 1999

(51) Int. Cl.$^7$ .................. A01N 59/16; A01N 59/20; B01J 21/00; B01J 23/00
(52) U.S. Cl. .................. 106/15.05; 106/18.32; 106/18.36; 424/618; 424/619; 424/630; 424/632; 424/633; 424/634; 424/635; 424/638; 502/240; 502/243; 502/244; 502/302; 502/324; 502/340; 502/341; 502/342; 502/343; 502/344; 502/345; 502/346; 502/347; 502/348; 502/349; 502/350; 502/351; 502/353
(58) Field of Search .................. 502/345, 346, 502/347, 348, 240, 243, 244, 302, 324, 340, 341, 342, 343, 344, 349, 350, 351, 353, 354, 355, 407, 411, 414, 415; 106/18.36, 15.05, 18.32; 424/618, 619, 630, 632, 633, 634, 635, 638

(56) References Cited

U.S. PATENT DOCUMENTS

| | | | |
|---|---|---|---|
| 2,915,365 A | 12/1959 | Saussol | 423/628 |
| 3,158,578 A | 11/1964 | Pons et al. | 252/436 |
| 3,222,129 A | 12/1965 | Osment et al. | 423/628 |
| 3,360,134 A | 12/1967 | Pullen | 210/502 |
| 3,485,771 A | 12/1969 | Horvath | 502/5 |
| 3,726,811 A | 4/1973 | Toombs et al. | 252/463 |
| 3,819,532 A | 6/1974 | Cracknell et al. | 252/447 |
| 3,875,125 A | 4/1975 | Whitehurst | 521/33 |
| 3,935,098 A | 1/1976 | Oda et al. | 210/38 |
| 3,945,945 A | 3/1976 | Kiovsky et al. | 252/463 |
| 3,958,341 A | 5/1976 | Podschus | 34/12 |
| 3,997,476 A | 12/1976 | Cull | 252/463 |
| 4,017,425 A | 4/1977 | Shiao | 242/453 |
| 4,051,072 A | 9/1977 | Bedford et al. | 252/464 |
| 4,125,457 A | 11/1978 | Brennan et al. | 208/254 |
| 4,126,582 A | 11/1978 | Diem et al. | 252/476 |
| 4,130,506 A | 12/1978 | Collier et al. | 252/438 |
| 4,166,100 A | 8/1979 | Vorobiev et al. | 423/626 |
| 4,177,139 A | 12/1979 | Hahn et al. | 210/33 |
| 4,248,741 A | * 2/1981 | Wernli et al. | 502/341 |

(List continued on next page.)

FOREIGN PATENT DOCUMENTS

| | | |
|---|---|---|
| AU | 9182630 A | 9/1992 |
| DE | 4404680 A1 | 2/1994 |
| EP | 206024 A | 12/1986 |
| EP | 0 224 375 A2 | 6/1987 |
| EP | 251783 A | 1/1988 |
| EP | 0 395 203 | 10/1990 |
| EP | 400349 A | 12/1990 |
| EP | 0425020 A1 | 5/1991 |
| EP | 505638 A1 | 9/1992 |
| EP | 0 525 631 A1 | 2/1993 |
| EP | 0526099 A1 | 2/1993 |
| EP | 665004 A2 | 8/1995 |
| EP | 673881 A1 | 9/1995 |
| EP | 722660 A2 | 7/1996 |
| EP | 732052 A2 | 9/1996 |
| FR | 2527197 | 5/1982 |
| GB | 604947 | 11/1945 |
| JP | 53-31599 | 3/1976 |
| JP | 53-31586 | 3/1978 |
| JP | 54-10288 | 1/1979 |

(List continued on next page.)

OTHER PUBLICATIONS

"Low temperature catalytic activity of cobalt oxide and ceria promoted Pt and Pd: —Influence of pretreatment and gas composition"; A. Torncrona, M. Skoglundh, P. Thormahlen, E. Fridell, E. Jobson; Applied Catalysis B: Environmental 14, pp. 131–146 (1997) (No month).

Badayova et al., "Antimicrobal & Bacteriostatic Treatment of Modified Polyamide Fibers," Vlakna Text 3(3), 108–110 (1996) (Abstract) (No month).*

"Low temperature catalytic activity of cobalt oxide and ceria promoted Pt and Pd: —Influence of pretreatment and gas composition"; A. Torncrona, M. Skoglundh, P. Thormahlen, E. Fridell, E. Jobson; Applied Catalysis B: Environmental 14, pp. 131–146 (1997) (No month).

Fukuzuka et al. Oxyacid Anion Adsorbent, 91: 9908p; *Chemical Abstracts*, vol. 91, 1979, p. 310, (No month).

Youssef et al. Oxidation of Carbon Monoxide Over Alumina–Supported Metal Oxide Catalysts, vol. 12, No. 4, pp. 335–343, 1995 (No month).

Sultan et al. Catalytic Dehydrogenation and Cracking of Cyclohexane over $Ni/Al_2O_3$ Solids, Adsorption Science & Technology, vol. 12, No. 1, pp. 1–6, 1996, (No month).

Jha et al. Chromatographic Utilization of the Sorption Behaviour of Some Nitrophenols on Acid–treated Alumina, Absorption Science & Technology, vol. 9, No. 2, pp. 92–108, 1992, (No month).

Ames et al., "Phosphorus Removal From Effluents in Alumina Columns," *J. Water Pollution Control Federation*, vol. 42, No. 5, Part 2, pp. R161–R172 (May 1970).

Batchelor et al., "A Surface Complex Model for Adsorption of Trace Components from Wastewater," *J. Water Pollution Control Federation*, vol. 59, No. 12, pp. 1059–1068 (Dec. 1987).

(List continued on next page.)

*Primary Examiner*—Anthony Green
(74) *Attorney, Agent, or Firm*—Needle & Rosenberg, P.C.

(57) ABSTRACT

The invention relates to a process for producing compositions containing a biocidal compound or adsorbent and/or catalyst compound and the compositions thereof. The invention also relates to a method for reducing or eliminating the amount of a bioactive agent or contaminant from an environment by contacting the environment with the composition of for a sufficient time to reduce or eliminate the amount of the bioactive agent or contaminant in the environment.

150 Claims, No Drawings

U.S. PATENT DOCUMENTS

| | | | |
|---|---|---|---|
| 4,279,782 A | 7/1981 | Chapman et al. | 252/465 |
| 4,292,968 A | 10/1981 | Ellis | 128/207.21 |
| 4,349,637 A | 9/1982 | Miedaner et al. | 501/126 |
| 4,353,741 A | 10/1982 | Capuano et al. | 75/109 |
| 4,393,311 A | 7/1983 | Feldman et al. | 250/459.1 |
| 4,396,512 A | 8/1983 | Beauman et al. | 210/668 |
| 4,407,865 A | 10/1983 | Nice | 427/217 |
| 4,411,041 A | 10/1983 | Braga | 15/167 R |
| 4,442,223 A | 4/1984 | Chester et al. | 502/68 |
| 4,499,208 A | 2/1985 | Fuderer | 502/415 |
| 4,504,387 A | 3/1985 | LeMire et al. | 210/100 |
| 4,507,257 A | 3/1985 | Fester et al. | 264/78 |
| 4,508,835 A | 4/1985 | Kaniuk et al. | 501/94 |
| 4,525,410 A | 6/1985 | Hagiwara et al. | 428/198 |
| 4,547,487 A | 10/1985 | Vogel et al. | 502/351 |
| 4,551,254 A | 11/1985 | Imada et al. | 210/688 |
| 4,558,031 A | 12/1985 | Ternan et al. | 502/388 |
| 4,579,839 A | 4/1986 | Pearson | 502/435 |
| 4,608,247 A | 8/1986 | Heinig, Jr. | 424/16 |
| 4,657,808 A | 4/1987 | Maggs | 428/263 |
| 4,764,394 A | 8/1988 | Conrad | 427/38 |
| 4,775,585 A | 10/1988 | Hagiwara et al. | 428/323 |
| 4,795,735 A | 1/1989 | Liu et al. | 502/415 |
| 4,835,338 A | 5/1989 | Liu | 585/823 |
| 4,843,034 A | 6/1989 | Herndon et al. | 437/189 |
| 4,849,223 A | 7/1989 | Pratt et al. | 424/409 |
| 4,874,596 A | 10/1989 | Lemelson | 423/446 |
| 4,885,065 A | 12/1989 | Gilgenbach | 204/157.6 |
| 4,902,666 A | 2/1990 | Rainis | 502/439 |
| 4,906,466 A | 3/1990 | Edwards et al. | 424/78 |
| 4,911,898 A | 3/1990 | Hagiwara et al. | 423/118 |
| 4,923,843 A | 5/1990 | Saforo et al. | 502/415 |
| 4,956,330 A * | 9/1990 | Elliott et al. | 502/326 |
| 4,980,067 A | 12/1990 | Hou et al. | 210/638 |
| 5,009,898 A | 4/1991 | Sakuma et al. | 424/618 |
| 5,053,374 A | 10/1991 | Absil et al. | 502/64 |
| 5,066,328 A | 11/1991 | Zlotnik | 106/18.32 |
| 5,078,902 A | 1/1992 | Antelman | 210/764 |
| 5,087,589 A | 2/1992 | Chapman et al. | 437/195 |
| 5,089,275 A | 2/1992 | Antelman | 424/602 |
| 5,098,582 A | 3/1992 | Antelman et al. | 210/759 |
| 5,133,871 A | 7/1992 | Levy | 210/638 |
| 5,147,686 A | 9/1992 | Ichimura et al. | 427/212 |
| 5,180,585 A | 1/1993 | Jacobson et al. | 424/405 |
| 5,198,118 A | 3/1993 | Heskett | 210/638 |
| 5,202,353 A | 4/1993 | Schrothe t al. | 514/500 |
| 5,204,070 A | 4/1993 | Wilson et al. | 422/186 |
| 5,212,131 A | 5/1993 | Belding | 502/60 |
| 5,217,626 A | 6/1993 | Yahya et al. | 210/764 |
| 5,218,179 A | 6/1993 | Matossian et al. | 219/121.43 |
| 5,227,358 A | 7/1993 | Takemura et al. | 502/316 |
| 5,236,471 A | 8/1993 | Van Dijen | 51/293 |
| 5,238,888 A | 8/1993 | Abe | 502/5 |
| 5,242,879 A | 9/1993 | Abe et al. | 502/180 |
| 5,244,648 A | 9/1993 | Dupin et al. | 423/626 |
| 5,244,667 A | 9/1993 | Hagiwara et al. | 424/405 |
| 5,244,855 A | 9/1993 | Morini et al. | 502/126 |
| 5,262,198 A | 11/1993 | Wu et al. | 427/249 |
| 5,326,567 A | 7/1994 | Capelli | 424/405 |
| 5,336,499 A | 8/1994 | Antelman | 424/405 |
| 5,346,722 A | 9/1994 | Beauseigneur et al. | 427/300 |
| 5,352,369 A * | 10/1994 | Heinig, Jr. | 210/760 |
| 5,366,948 A | 11/1994 | Absil et al. | 502/68 |
| 5,409,467 A | 4/1995 | Raad et al. | 604/265 |
| 5,413,788 A | 5/1995 | Edwards et al. | 424/409 |
| 5,414,204 A | 5/1995 | Hosono et al. | 588/210 |
| 5,415,770 A | 5/1995 | Heskett | 210/202 |
| 5,422,323 A | 6/1995 | Banerjee et al. | 501/100 |
| 5,427,995 A | 6/1995 | Ziebarth et al. | 502/411 |
| 5,432,077 A | 7/1995 | Farrah | 435/244 |
| 5,441,717 A | 8/1995 | Ohsumi et al. | 423/306 |
| 5,476,881 A | 12/1995 | Suh | 523/122 |
| 5,503,840 A | 4/1996 | Jacobson et al. | 424/421 |
| 5,510,306 A | 4/1996 | Murray | 502/64 |
| 5,510,560 A | 4/1996 | O'Young et al. | 585/671 |
| 5,516,480 A | 5/1996 | Krall et al. | 264/343 |
| 5,516,962 A | 5/1996 | Chu et al. | 585/722 |
| 5,520,664 A | 5/1996 | Bricault, Jr., et al. | 604/265 |
| 5,560,876 A | 10/1996 | Boulanger et al. | 264/40.1 |
| 5,571,520 A | 11/1996 | Antelman | 424/405 |
| 5,595,750 A | 1/1997 | Jacobson et al. | 424/421 |
| 5,633,422 A | 5/1997 | Murray | 585/671 |
| 5,648,585 A | 7/1997 | Murray et al. | 585/671 |
| 5,665,668 A * | 9/1997 | Grigorova et al. | 502/344 |
| 5,698,488 A * | 12/1997 | Birbara et al. | 502/325 |
| 5,753,250 A | 5/1998 | Hagiwara | 424/405 |
| 5,772,896 A * | 6/1998 | Denkewicz, Jr. et al. | 210/754 |
| 5,817,325 A | 10/1998 | Sawan et al. | 424/411 |
| 5,824,267 A | 10/1998 | Kawasumi et al. | 422/28 |
| 5,827,524 A | 10/1998 | Hagiwara et al. | 424/405 |
| 5,849,311 A | 12/1998 | Sawan et al. | 424/406 |
| 5,858,246 A * | 1/1999 | Rafter et al. | 210/754 |
| 5,863,548 A | 1/1999 | Elder | 424/408 |
| 5,869,073 A | 2/1999 | Sawan et al. | 424/406 |
| 5,876,489 A | 3/1999 | Kunisaki et al. | 96/226 |
| 5,935,609 A * | 8/1999 | Denkewicz, Jr. et al. | 21/748 |
| 6,022,823 A * | 2/2000 | Augustine et al. | 502/243 |
| 6,030,537 A | 2/2000 | Shaniuk et al. | 210/683 |
| 6,030,632 A | 2/2000 | Sawan et al. | 424/405 |
| 6,093,422 A * | 7/2000 | Denkewicz, Jr. et al. | 424/618 |
| 6,107,354 A | 8/2000 | Shaniuk et al. | 521/28 |
| 6,217,780 B1 * | 4/2001 | Denkewicz, Jr. et al. | 210/764 |
| 6,254,894 B1 * | 7/2001 | Denkewicz, Jr. et al. | 424/618 |

FOREIGN PATENT DOCUMENTS

| | | | |
|---|---|---|---|
| JP | 54-28287 | | 3/1979 |
| JP | 54141375 | | 11/1979 |
| JP | 56121637 | A2 | 9/1981 |
| JP | 56121637 | | 9/1981 |
| JP | 61233065 | A2 | 10/1981 |
| JP | 57171435 | | 10/1982 |
| JP | 58156349 | | 9/1983 |
| JP | 60255681 | | 12/1985 |
| JP | 08157314 | A2 | 6/1986 |
| JP | 63062546 | | 3/1988 |
| JP | 63307807 | A | 12/1988 |
| JP | 1164781 | A | 6/1989 |
| JP | 1316303 | A | 12/1989 |
| JP | 2101003 | | 4/1990 |
| JP | 2215704 | A | 8/1990 |
| JP | 3066738 | A | 3/1991 |
| JP | 3255009 | A | 11/1991 |
| JP | 3275627 | A | 12/1991 |
| JP | 03287508 | A2 | 12/1991 |
| JP | 4012041 | A | 1/1992 |
| JP | 04020347 | A2 | 1/1992 |
| JP | 4-23577 | | 4/1992 |
| JP | 4124102 | A | 4/1992 |
| JP | 4145007 | A | 5/1992 |
| JP | 04288006 | A2 | 10/1992 |
| JP | 05000154 | A2 | 1/1993 |
| JP | 5201817 | A | 8/1993 |
| JP | 5229911 | A | 9/1993 |
| JP | 6056613 | A | 3/1994 |
| JP | 6080528 | A | 3/1994 |
| JP | 6122617 | A | 5/1994 |
| JP | 6272173 | A | 9/1994 |
| JP | 6303920 | A | 11/1994 |
| JP | 06305906 | A2 | 11/1994 |
| JP | 07033616 | A2 | 2/1995 |
| JP | 07033617 | A2 | 2/1995 |

| | | |
|---|---|---|
| JP | 7196424 A | 8/1995 |
| JP | 7291758 A | 11/1995 |
| JP | 8012512 A | 1/1996 |
| JP | 08059404 A2 | 3/1996 |
| JP | 8073702 A | 3/1996 |
| JP | 08119814 A2 | 5/1996 |
| JP | 08119821 A2 | 5/1996 |
| JP | 8133919 A | 5/1996 |
| JP | 8150334 A | 6/1996 |
| JP | 8151037 A | 6/1996 |
| JP | 8165208 A | 6/1996 |
| JP | 8176961 A | 7/1996 |
| JP | 09157118 A2 | 6/1997 |
| JP | 09157119 A2 | 6/1997 |
| JP | 09165310 A2 | 6/1997 |
| JP | 09249511 A2 | 9/1997 |
| JP | 9267070 A | 10/1997 |
| JP | 10025215 A | 1/1998 |
| JP | 10025216 A | 1/1998 |
| JP | 10025435 A | 1/1998 |
| JP | 10045562 A | 2/1998 |
| JP | 10088390 A | 4/1998 |
| JP | 10113612 A | 5/1998 |
| JP | 10130885 A | 5/1998 |
| JP | 10176097 A | 6/1998 |
| JP | 10192627 A | 7/1998 |
| JP | 10217128 A | 8/1998 |
| JP | 10264297 A | 10/1998 |
| JP | 10265959 A | 10/1998 |
| JP | 11012692 A | 1/1999 |
| JP | 11029184 A | 2/1999 |
| PL | 158880 | 9/1990 |
| PL | 159625 * | 9/1990 |
| RO | 98720 A | 4/1990 |
| WO | WO 9415463 A1 | 7/1994 |
| WO | WO 94/26661 | 11/1994 |
| WO | WO 96/17682 | 6/1996 |
| WO | WO 96/33013 | 10/1996 |
| WO | WO 9723594 A | 7/1997 |
| WO | WO 97/47380 | 12/1997 |
| WO | WO 9813530 A1 | 4/1998 |

OTHER PUBLICATIONS

Brattebo et al., "Phosphorus Removal By Granular Activated Alumina," *Wat.Res.,* vol. 20, No. 8, pp. 977–986 (1986) (No month).

Huang, "Removal of Phosphate By Powdered Aluminum Oxide Adsorption," *J. Water Pollution Control Federation,* vol. 7, pp. 1811–1817 (Aug. 1977).

Gangoli et al., "Phosphate Adsorption Studies," *J. Water Pollution Control Federation,* vol. 45, No. 5, pp. 842–849 (May 1973).

Gangoli et al., "Kinetics of Phosphate Adsorption on Alumina and Fly Ash," vol. 46, No. 8, pp. 2035–2042 (Aug. 1974).

Neufeld et al., "Removal of Orthophosphates form Aqueous Solutions with Activated Alumina," *Environmental Science and Technology,* vol. 3, No. 7, pp. 661–667 (Jul. 1969).

Shiao et al., "Phosphate Removal from Aqueous Solution from Activated Red Mud," *J. Water Pollution Control Federation,* vol. 49, pp. 280–285 (Feb. 1977).

Urano et al., "Process Development for Removal and Recovery of Phosphorus from Wastewater by a New Adsorbent. 1. Preparation Method and Adsorption Capability of a New Adsorbent," *Ind.Eng.Chem.Res.,* vol. 30, No. 8, pp. 1893–1896 (1991) (No month).

Urano et al., "Process Development for Removal and Recovery of Phosphorus from Wastewater by a New Adsorbent. 2. Adsorption Rates and Breakthrough Curves," *Ind.Eng.Chem.Res.,* vol. 30, No. 8, pp. 1897–1899 (1991) (No month).

Winkler et al., "Kinetics of Orthophosphate Removal from Aqueous Solutions by Activated Alumina," *J. Water Pollution Control Federation,* vol. 43, No. 3, Part 1, pp. 474–482 (Mar. 1971).

Yee, "Selective Removal of Mixed Phosphates by Activated Alumina," *J.Amer. Water Works Assoc.,* vol. 58, pp. 239–247 (1966) (No month).

* cited by examiner

COMPOSITIONS CONTAINING A BIOCIDAL COMPOUND OR AN ADSORBENT AND/OR CATALYST COMPOUND AND METHODS OF MAKING AND USING THEREFOR

BACKGROUND OF THE INVENTION

1. Field of the Invention

This invention relates generally to compositions containing a biocidal compound or an adsorbent and/or catalyst compound and methods of making and using therefor.

2. Background Art

The use of certain metal ions as antibacterial and antimicrobial agents are known in the art. For example, silver ions, copper ions, and zinc ions are useful antimicrobial agents. Typically, these metal ions are incorporated into a support system, wherein the support material ultimately releases the antimicrobial agent into an environment containing the microbial agent.

Typically, the process for preparing the antimicrobial/support system generally involves contacting the support material with a solution containing the metal ion that possesses antimicrobial activity, then drying the resultant particle. Examples of this process are disclosed in Japanese Patent Application No. 3275627; Japanese Patent Application No. 5201817; Japanese Patent Application No. 6056613; Japanese Patent Application No. 6080528; Japanese Patent Application No. 6272173; Japanese Patent Application No. 8165208; Japanese Patent Application No. 9267070; Japanese Patent Application No. 10130885; International Application No. WO 9723594 to Walker; U.S. Pat. No. 5,827,524 to Hagiwara et al.; U.S. Pat. No. 4,504,387 to LeMire et al.; and U.S. Pat. No. 5,441,717 to Ohsumi et al. A disadvantage of this process is that the antimicrobial compound rapidly deadsorbs from the support, which results in reduced biocidal activity over time as well as the introduction of high levels of the antimicrobial compound into the environment.

Another process for incorporating silver into a support material involves the addition of a reducing agent to a mixture composed of the support material and a silver salt. The process results in the in situ reduction of the silver salt. U S. Pat. No. 4,396,512 to Beauman et al.; U S. Pat. No. 5,824,267 to Kawasumi et al.; U S. Pat. No. 4,407,865 to Nice; U S. Pat. No. 4,130,506 to Collier et al.; U S. Pat. No. 4,126,582 to Diem et al.; and U S. Pat. No. 4,353,741 to Capuano et al. disclose the in situ reduction of a silver salt. None of these patents, however, disclose nor appreciate the benefits of drying and/or heating the support and the silver salt prior to contacting with the reducing agent.

There has been a need in the art for compositions that can release a biocidal compound at a desired rate that is dependent upon the bioactive agent that is to be reduced or eliminated from an environment. There is also a need for compositions that can reduce or eliminate a bioactive agent in an environment for an extended period of time. Additionally, there is also a need for compositions that can reduce or eliminate a wide variety of bioactive contaminants. Finally, there is a need for compositions that can reduce or eliminate a bioactive agent in an environment that is present in high concentrations.

There is also a need for compositions that contain an adsorbent and/or catalyst compound that can reduce or eliminate a variety of contaminants over an extended period of time from an environment.

Applicants have developed new methods for preparing compositions containing a biocidal compound or an adsorbent and/or catalyst particle that address the needs described above. None of the above-cited documents disclose the compositions or processes such as those described and claimed herein.

SUMMARY OF THE INVENTION

In accordance with the purpose(s) of this invention, as embodied and broadly described herein, this invention, in one embodiment, relates to a process for producing a composition containing a biocidal compound, comprising:
(a) admixing a support with a first biocidal compound to produce a mixture;
(b) heating the mixture produced in step (a) at from 80 to 1,800° C. to produce a heated mixture; and
(c) contacting the heated mixture produced in step (b) with a reducing agent to reduce at least some of the first biocidal compound to produce a first reduced biocidal/support composition.

The invention further relates to a process for producing a composition containing a biocidal compound comprising:
(a) admixing a support with a first biocidal compound to produce a mixture;
(b) heating the mixture produced in step (a) at from 80 to 1,800° C. to produce a heated mixture;
(c) contacting the heated mixture produced in step (b) with a reducing agent to reduce at least some of the first biocidal compound to produce a first reduced biocidal/support composition; and
(d) oxidizing at least some of the first biocidal compound in the first reduced biocidal/support composition to produce a first oxidized biocidal/support composition.

The invention further relates to a process for producing a composition containing a biocidal compound, comprising:
(a) admixing a support with a biocidal compound to produce a mixture;
(b) drying the mixture to produce a dried mixture; and
(c) contacting the dried mixture produced in step (b) with a reducing agent to reduce at least some of the biocidal compound to produce a reduced biocidal/support composition.

The invention further relates to a process for producing a composition containing a biocidal compound comprising:
(a) admixing components comprising:
   (1) a support;
   (2) a binder comprising a colloidal metal oxide or colloidal metalloid oxide;
   (3) a first biocidal compound; and
   (4) an acid;
(b) removing a sufficient amount of water to cross-link the binder with itself, the support, and/or the first biocidal compound to produce a first binder/biocidal composition; and
c) contacting the first binder/biocidal composition produced in step (b) with a reducing agent to reduce at least some of the first biocidal compound to produce a first reduced biocidal/support composition.

The invention further relates to a process for producing a composition containing a biocidal compound comprising:
(a) admixing components comprising:
   (i) a binder comprising a colloidal metal oxide or colloidal metalloid oxide,
   (ii) a support, and
   (iii) an acid,
(b) removing a sufficient amount of water from the mixture to cross-link the binder with itself and/or the support to produce a binder/support system; and (c) admixing the binder/support system produced in step (b) with a first biocidal compound to produce a first binder/biocidal composition.

The invention further relates to a process for producing a composition containing an adsorbent and/or catalyst compound, comprising:
(a) admixing a support with a first adsorbent and/or catalyst compound to produce a mixture;
(b) heating the mixture produced in step (a) at from 80 to 1,800° C. to produce a heated mixture; and
c) contacting the heated mixture produced in step (b) with a reducing agent to reduce at least some of the first adsorbent and/or catalyst compound to produce a first reduced adsorbent and/or catalyst/support composition.

The invention further relates to a process for producing a composition containing an adsorbent and/or catalyst compound comprising:
a) admixing a support with a first adsorbent and/or catalyst compound to produce a mixture;
(b) heating the mixture produced in step (a) at from 80 to 1,800° C. to produce a heated mixture;
(c) contacting the heated mixture produced in step (b) with a reducing agent to reduce at least some of the first adsorbent and/or catalyst compound to produce a first reduced adsorbent and/or catalyst/support composition; and
(d) oxidizing at least some of the first adsorbent and/or catalyst compound in the first reduced adsorbent and/or catalyst/support composition to produce a first oxidized adsorbent and/or catalyst/support composition.

The invention further relates to a process for producing a composition containing an adsorbent and/or catalyst compound, comprising:
(a) admixing a support with an adsorbent and/or catalyst compound to produce a mixture;
(b) drying the mixture to produce a dried mixture; and
(c) contacting the dried mixture produced in step (b) with a reducing agent to reduce at least some of the adsorbent and/or catalyst compound to produce a reduced adsorbent and/or catalyst compound/support composition.

The invention further relates to a process for producing a composition containing an adsorbent and/or catalyst compound comprising:
(a) admixing components comprising:
  (1) a support;
  (2) a binder comprising a colloidal metal oxide or colloidal metalloid oxide;
  (3) a first adsorbent and/or catalyst compound; and
  (4) an acid;
(b) removing a sufficient amount of water to cross-link the binder with itself, the support, and/or the adsorbent and/or catalyst compound to produce a first binder/adsorbent and/or catalyst composition; and
(c) contacting the first binder/adsorbent and/or catalyst composition produced in step (b) with a reducing agent to reduce at least some of the first adsorbent and/or catalyst compound to produce a first reduced adsorbent and/or catalyst/support composition.

The invention further relates to a process for producing a composition containing an adsorbent and/or catalyst compound comprising:
(a) admixing components comprising:
  (i) a binder comprising a colloidal metal oxide or colloidal metalloid oxide,
  (ii) a support, and
  (iii) an acid, b) removing a sufficient amount of water from the mixture to cross-link the binder with itself and/or the support to produce a binder/support system; and
(c) admixing the binder/support system produced in step (b) with a first adsorbent and/or catalyst compound to produce a first binder/adsorbent and/or catalyst composition.

The invention further relates to the compositions produced by the processes of the present invention.

The invention further relates to a method for reducing or eliminating the amount of a bioactive agent from an environment, comprising contacting the environment with the composition produced by the process of the present invention for a sufficient time to reduce or eliminate the amount of the bioactive agent in the environment.

The invention further relates to a method for reducing or eliminating the amount of a contaminant from an environment, comprising contacting the environment with the composition produced by the process of the present invention for a sufficient time to reduce or eliminate the amount of the contaminant in the environment.

The invention further relates to a method for reducing or eliminating the amount of a bioactive agent from an environment, comprising contacting the environment with a biocidal compound system, wherein the biocidal compound system comprises:
(a) a first layer comprising a scavenger, wherein the first layer has a first surface and a second surface, and
b) a second layer comprising the composition produced by the process of the present invention, wherein the second layer has a first surface and a second surface,
wherein the first surface of the first layer is adjacent to and in contact with the first surface of the second layer,
for a sufficient time to reduce or eliminate the amount of the bioactive agent in the environment.

The invention further relates to a method for reducing or eliminating the amount of a bioactive agent from an environment, comprising contacting the environment with a biocidal compound system, wherein the biocidal compound system comprises:
(a) a first layer comprising the composition produced by the process comprising:
  (i) admixing a first support with a first biocidal compound to produce a mixture;
  (ii) heating the mixture produced in step (i) at from 80 to 1,800° C. to produce a heated mixture;
  (iii) contacting the heated mixture produced in step (ii) with a reducing agent to reduce at least some of the first biocidal compound to produce a first reduced biocidal/support composition; and
  (iv) oxidizing at least some of the first biocidal compound in the first reduced biocidal/support composition to produce a first oxidized biocidal/support composition,
wherein the first layer has a first surface and a second surface, and
(b) a second layer comprising the composition produced by the process comprising:
  (v) admixing a second support with a second biocidal compound to produce a mixture;
  (vi) heating the mixture produced in step (v) at from 80 to 1,800° C. to produce a heated mixture; and
  (vii) contacting the heated mixture produced in step (vii) with a reducing agent to reduce at least some of the second biocidal compound to produce a second reduced biocidal/support composition,
wherein the first surface of the first layer is adjacent to and in contact with the first surface of the second layer, for a sufficient time to reduce or eliminate the amount of the bioactive agent in the environment.

The invention further relates to a method for reducing or eliminating the amount of a bioactive agent from an environment, comprising contacting the environment with a biocidal compound system, wherein the biocidal compound system comprises:

(I) a first layer comprising a binder composition, wherein the binder composition is produced by the method comprising
 (i) mixing components comprising
  (a) a binder comprising a colloidal metal oxide or colloidal metalloid oxide,
  (b) an oxide adsorbent and/or catalyst particle, and
  (c) an acid, and
 (ii) removing a sufficient amount of water from the mixture to cross-link the binder with itself and/or component b to form a binder composition,
 wherein the first layer has a first surface and a second surface, and
(II) a second layer comprising the composition produced by the process of the present invention, wherein the second layer has a first surface and a second surface,
wherein the first surface of the first layer is adjacent to and in contact with the first surface of the second layer, for a sufficient time to reduce or eliminate the amount of the bioactive agent in the environment.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE PREFERRED EMBODIMENTS

The present invention may be understood more readily by reference to the following detailed description of preferred embodiments of the invention and the Examples included therein.

Before the present compositions of matter and methods are disclosed and described, it is to be understood that this invention is not limited to specific synthetic methods or to particular formulations, as such may, of course, vary. It is also to be understood that the terminology used herein is for the purpose of describing particular embodiments only and is not intended to be limiting.

In this specification and in the claims which follow, reference will be made to a number of terms which shall be defined to have the following meanings:

The singular forms "a," "an" and "the" include plural referents unless the context clearly dictates otherwise.

The term "ppm" refers to parts per million and the term "ppb" refers to parts per billion.

The term "CFU" refers to colony forming units.

"Optional" or "optionally" means that the subsequently described event or circumstance may or may not occur, and that the description includes instances where the event or circumstance occurs and instances where it does not.

The term "composition" as used herein is a system that is prepared from and is composed of two or more different components.

In accordance with the purpose(s) of this invention, as embodied and broadly described herein, this invention, in one embodiment, relates to a process for producing a composition containing a biocidal compound, comprising:

(a) admixing a support with a first biocidal compound to produce a mixture;
(b) heating the mixture produced in step (a) at from 80 to 1,800° C. to produce a heated mixture; and
(c) contacting the heated mixture produced in step (b) with a reducing agent to reduce at least some of the first biocidal compound to produce a first reduced biocidal/support composition.

The compositions produced by this process are referred to herein as "Group I compositions."

The invention further relates to a process for producing a composition containing a biocidal compound comprising:

(a) admixing a support with a first biocidal compound to produce a mixture;
(b) heating the mixture produced in step (a) at from 80 to 1,800° C. to produce a heated mixture;
(c) contacting the heated mixture produced in step (b) with a reducing agent to reduce at least some of the first biocidal compound to produce a first reduced biocidal/support composition; and
(d) oxidizing at least some of the first biocidal compound in the first reduced biocidal/support composition to produce a first oxidized biocidal/support composition.

The compositions produced by this process are referred to herein as "Group II compositions."

The invention further relates to a process for producing a composition containing a biocidal compound, comprising:

(a) admixing a support with a biocidal compound to produce a mixture;
(b) drying the mixture to produce a dried mixture; and
(c) contacting the dried mixture produced in step (b) with a reducing agent to reduce at least some of the biocidal compound to produce a reduced biocidal/support composition.

The compositions produced by this process are referred to herein as "Group III compositions."

The invention further relates to a process for producing a composition containing a biocidal compound comprising:

a) admixing components comprising:
  (1) a support;
  (2) a binder comprising a colloidal metal oxide or colloidal metalloid oxide;
  (3) a first biocidal compound; and
  (4) an acid;
(b) removing a sufficient amount of water to cross-link the binder with itself, the support, and/or the first biocidal compound to produce a first binder/biocidal composition; and
(c) contacting the first binder/biocidal composition produced in step (b) with a reducing agent to reduce at least some of the first biocidal compound to produce a first reduced biocidal/support composition.

The compositions produced by this process are referred to herein as "Group IV compositions."

The invention further relates to a process for producing a composition containing a biocidal compound comprising:

(a) admixing components comprising:
  (i) a binder comprising a colloidal metal oxide or colloidal metalloid oxide,
  (ii) a support, and
  (iii) an acid,
(b) removing a sufficient amount of water from the mixture to cross-link the binder with itself and/or the support to produce a binder/support system; and (c) admixing the binder/support system produced in step (b) with a first biocidal compound to produce a first binder/biocidal composition.

The compositions produced by this process are referred to herein as "Group V compositions."

The invention further relates to a process for producing a composition containing an adsorbent and/or catalyst compound, comprising:
(a) admixing a support with a first adsorbent and/or catalyst compound to produce a mixture;
(b) heating the mixture produced in step (a) at from 80 to 1,800° C. to produce a heated mixture; and
(c) contacting the heated mixture produced in step (b) with a reducing agent to reduce at least some of the first adsorbent and/or catalyst compound to produce a first reduced adsorbent and/or catalyst/support composition.

The compositions produced by this process are referred to herein as "Group VI compositions."

The invention further relates to a process for producing a composition containing an adsorbent and/or catalyst compound comprising:
(a) admixing a support with a first adsorbent and/or catalyst compound to produce a mixture;
(b) heating the mixture produced in step (a) at from 80 to 1,800° C. to produce a heated mixture;
(c) contacting the heated mixture produced in step (b) with a reducing agent to reduce at least some of the first adsorbent and/or catalyst compound to produce a first reduced adsorbent and/or catalyst/support composition; and
(d) oxidizing at least some of the first adsorbent and/or catalyst compound in the first reduced adsorbent and/or catalyst/support composition to produce a first oxidized adsorbent and/or catalyst/support composition.

The compositions produced by this process are referred to herein as "Group VII compositions."

The invention further relates to a process for producing a composition containing an adsorbent and/or catalyst compound, comprising:
(a) admixing a support with an adsorbent and/or catalyst compound to produce a mixture;
(b) drying the mixture to produce a dried mixture; and
(c) contacting the dried mixture produced in step (b) with a reducing agent to reduce at least some of the adsorbent and/or catalyst compound to produce a reduced adsorbent and/or catalyst compound/support composition.

The compositions produced by this process are referred to herein as "Group VIII compositions."

The invention further relates to a process for producing a composition containing an adsorbent and/or catalyst compound comprising:
(a) admixing components comprising:
  (1) a support;
  (2) a binder comprising a colloidal metal oxide or colloidal metalloid oxide;
  (3) a first adsorbent and/or catalyst compound; and
  (4) an acid;
(b) removing a sufficient amount of water to cross-link the binder with itself, the support, and/or the adsorbent and/or catalyst compound to produce a first binder/adsorbent and/or catalyst composition; and
(c) contacting the first binder/adsorbent and/or catalyst composition produced in step (b) with a reducing agent to reduce at least some of the first adsorbent and/or catalyst compound to produce a first reduced adsorbent and/or catalyst/support composition.

The compositions produced by this process are referred to herein as "Group IX compositions."

The invention further relates to a process for producing a composition containing an adsorbent and/or catalyst compound comprising:
(a) admixing components comprising:
  (i) a binder comprising a colloidal metal oxide or colloidal metalloid oxide,
  (ii) a support, and
  (iii) an acid,
(b) removing a sufficient amount of water from the mixture to cross-link the binder with itself and/or the support to produce a binder/support system; and
(c) admixing the binder/support system produced in step (b) with a first adsorbent and/or catalyst compound to produce a first binder/adsorbent and/or catalyst composition.

The compositions produced by this process are referred to herein as "Group X compositions."

The invention further relates to the compositions produced by the processes of the present invention.

The support can be any material that can absorb and/or adsorb a biocidal compound when the biocidal compound is admixed with the support. The support can be any material that can absorb and/or adsorb an adsorbent and/or catalyst compound when the adsorbent and/or catalyst compound is admixed with the support. Examples of supports useful in the present invention include, but are not limited to, a polymer, carbon, a cellulosic fiber, or a metal oxide.

Any of the polymers disclosed in U.S. Pat. No. 4,775,585 to Hagiwara et al., which is incorporated herein by this reference in its entirety, can be used in the present invention. In one embodiment, the polymer comprises synthetic or semi-synthetic organic polymers. Examples of organic polymers include, but are not limited to, polyethers, such as polyethylene oxide; thermoplastic synthetic polymers, such as polyethylene, polypropylene, polystyrene, polyvinyl chloride, polyvinylidene chloride, polyamides, polyesters, polyvinyl alcohol, polycarbonates, polyacetals, ABS resins, acrylic resins, fluorine-contained resins, polyurethane elastomers, polyester elastomers; thermosetting synthetic polymers, such as phenolic resins, urea resins, and urethane resins; or regenerated or semi-synthetic polymers, such as rayon, cuprammonium rayon, acetate rayon, triacetate rayon. In another embodiment, the polymer comprises Nylon 6, Nylon 66, polyvinyl alcohol, polyvinyl chloride, polyvinylidene chloride, polyethylene terephthalate, polybutylene terephthalate, polyacrylonitrile, polyethylene, polypropylene and copolymers thereof; regenerated or semi-synthetic polymers such as rayon, cuprammonium rayon, acetate rayon, and triacetate rayon.

Examples of cellulosic fibers include paper and wood products. The cellulosic fibers disclosed in U.S. Pat. No. 4,396,512 to Beuaman et al., which is herein incorporated by this reference in its entirety, can be used in the present invention.

Any metal oxide known in the art can be used as the support in the present invention. Examples of such metal oxides include, but are not limited to, oxide complexes, such as transition metal oxides, lanthanide oxides, as well as oxides of Group IIA (Mg, Ca, Sr, Ba), Group IIIA (B, Al, Ga, In, Tl), Group IVA (Si, Ge, Sn, Pb), and Group VA (As, Sb, Bi). In another embodiment, the metal oxide comprises an oxide of aluminum, titanium, copper, vanadium, silicon, manganese, iron, zinc, zirconium, magnesium, thorium, or a combination thereof. Typically, any oxidation state of the metal oxide may be useful for the present invention. The metal oxide can be a mixture of at least two metal oxide particles having the same metal with varying stoichiometry and oxidation states. In one embodiment, the metal oxide comprises $Al_2O_3$, $TiO_2$, $CuO$, $Cu_2O$, $V_2O_5$, $SiO_2$, $MnO_2$, $Mn_2O_3$, $Mn_3O_4$, $ZnO$, $MgO$, $ThO_2$, $Fe_2O_3$, $Fe_3O_4$, or zeolite. In a preferred embodiment, the support is aluminum oxide, silicon dioxide, or an oxide magnesium, more preferably aluminum oxide.

In a further embodiment, the metal oxide further comprises a second type of an oxide of aluminum, titanium, copper, vanadium, silicon, manganese, iron, zinc, zirconium, magnesium, thorium, or a combination thereof. In another embodiment, the metal oxide further comprises a second type of particles of aluminum oxide, titanium dioxide, copper oxide, vanadium pentoxide, silicon dioxide, manganese dioxide, iron oxide, zinc oxide, or zeolite. Typical zeolites used in the present invention include "Y" type, "beta" type, mordenite, and ZsM5. In one embodiment, the support comprises aluminum oxide, silicon dioxide, or an oxide of magnesium, preferably aluminum oxide.

In another embodiment, the metal oxide comprises an adsorbent and/or catalyst compound. When the metal oxide acts as an adsorbent, the metal oxide can adsorb a large amount of bioactive agent or contaminant from the environment. When the metal oxide is an adsorbent, the bioactive agent or the contaminant is chemically bond to and very tightly retained in the metal oxide. These chemical bonds are ionic and/or covalent in nature. In one embodiment, when the metal oxide comprises an adsorbent and/or catalyst compound, the metal oxide can be regenerated using techniques known in the art. In another embodiment, when the support comprises a metal oxide, the metal oxide absorbs the bioactive agent or contaminant from the environment.

When the metal oxide behaves as a catalyst, the metal oxide can catalytically decompose or remediate a contaminant in the environment. The catalytic reaction can be at room temperature for certain applications.

In one embodiment, the support is heated from 80 to 1,800° C. prior to admixing the support with the first biocidal compound. In various embodiments, the lower limit of the heating temperature is 80, 100, 150, 200, 250, 300, 350, 400, 450, 500, 600, 700, 800, 900, or 1,000° C., and the upper limit of the heating temperature is 550, 600, 650, 700, 750, 800, 850, 900, 950, 1,000, 1,100, 1,200, 1,300, 1,400, 1,500, 1,600, or 1,700° C. In one embodiment, when the support is a metal oxide, the metal oxide comprises calcined or sintered aluminum oxide that was produced by calcining or sintering the precursor to the aluminum oxide at a particle temperature of from 200° C. to 1,800° C. The precursor to the calcined or sintered aluminum oxide can include but is not limited to boehmite, bauxite, pseudo-boehmite, scale, $Al(OH)_3$, and alumina hydrates.

In another embodiment, the metal oxide is acid treated prior to admixing with the first biocidal compound. All of the metal oxides disclosed above can be acid treated. The acid activation or enhancement treatment process disclosed in international publication no. WO 97/47380 entitled "Acid Contacted Enhanced Adsorbent Particle and/or Catalyst and Binder System," which is herein incorporated by this reference in its entirety, can be used in the present invention to prepare the acid treated metal oxide.

The acid that can be used in this invention can be any acid or mixture of acids that can promote the formation of hydroxyl groups onto the surface of the pores of the metal oxide. Examples of such acids include, but are not limited to, nitric acid, sulfuric acid, hydrochloric acid, boric acid, acetic acid, formic acid, phosphoric acid, and mixtures thereof. In a preferred embodiment, the acid is acetic acid because it is relatively safer to handle than most other acids and because of its cost effectiveness.

In one embodiment, the acid is diluted with water to prevent dissolution of the metal oxide. In general, only a dilute solution of the acid is required to achieve maximum or saturated loading of the ion moieties on the metal oxide. For example, a 0.5 wt. % (0.09 N; pH of about 2.9) and even a 0.1 wt. % (0.02 N; pH of about 3.25) acetic acid solution has been found effective. However, a wide range of concentrations of acid can be used in this invention from very dilute to very concentrated depending on the hazards involved and the economics of production. However, if the acid is too concentrated, it will etch the metal oxide and increase the number of macropores while eliminating micropores, which is detrimental to the particles of this invention. Thus, the acid treatment is preferably of a concentration (i.e. acid strength as measured by, e.g., normality or pH), acid type, temperature and length of time to be more than a mere surface wash but less than an etching. In particular embodiments, the etching of the metal oxide is minimized or is only nominal by selection of the acid treatment conditions, such as acid strength, acid type, and temperature and time of treatment, such that the reduction in overall surface area, as preferably measured by the BET method, is less than 20%, less than 15%, less than 10%, less than 5%, less than 2%, less than 1%, or less than 0.5%. Strong acids, such as for example hydrochloric acid, nitric acid or sulfuric acid, should preferably be used at a concentration or strength lower than a weak acid, such as for example acetic acid, because the strong acid tends to chemically react with and etch the metal oxide to a much greater degree than a weak acid of comparable concentration.

In a particular embodiment, the acid is of an upper strength equivalent to a 0.5 N (normality) aqueous solution of acetic acid. In other embodiments, the upper strength of the acid is equivalent to a 0.25 N, 0.1 N, 0.09 N, 0.075 N, 0.05 N, 0.02 N, 0.01 N, 0.005 N or 0.001 N aqueous acetic acid solution. The lower strength of the acid should be that which provides more than a surface washing but imparts enhanced adsorbent effects to the metal oxide. In particular embodiments, the lower strength of the acid is equivalent to a 0.25 N, 0.1 N, 0.09 N, 0.075 N, 0.05 N, 0.02 N, 0.01 N, 0.005 N, 0.001 N, 0.0005 N, or 0.0001 N aqueous acetic acid solution.

After acid treatment, the resultant metal oxide substantially retains the micropores originally present and the acid does not etch the particle to any appreciable degree and does not create any appreciable amount of new macropores (median pore diameter greater than about 35 nm). In a preferred embodiment, when the metal oxide is aluminum oxide, the acid treated aluminum oxide maintains its microporous nature, having a median pore size of 3.5 nm to 35 nm diameter and a BET surface area of from 120 to 350 m2/g.

Additionally, the acid preferably has some water present to provide OH and/or $H^+$ ions, which bond with the metal oxide. When the acid is diluted with water, the water is preferably distilled water to minimize the amount of impurities contacting the metal oxide during acid treatment.

Typically, the acid enhanced metal oxide is made by the following process. The metal oxide can be contacted with the acid by various means, including the metal oxide being dipped in, extensively washing with, or submerged in the acid. The length of time the metal oxide is be contacted with the acid varies according to the ability of the particular metal oxide to generate hydroxyl groups on the surface and pores of the particle. The time can be as low as 30 seconds, a few (three) minutes, at least 15 minutes, at least one hour, at least 6 hours, at least 12 hours, or at least one day, to achieve adequate adsorption results and/or to preferably assure saturation. The time must be sufficient to at least increase the number of hydroxyl groups on the metal oxide. In one embodiment, the metal oxide is submerged in the acid, and saturation is typically complete when there is complete adsorption of the metal oxide pores with the acid solution. The contacting should be substantial enough to provide penetration of the acid throughout the pores of the metal oxide thereby increasing the number of hydroxyl groups on the pore surface of the particle. Mere washing the outside surface of the metal oxide to remove impurities is not sufficient to provide adequate penetration of the acid into and throughout the pores of the metal oxide.

Typically, the acid contacting is preformed at room temperature. The higher the acid temperature and concentration, the more likely the acid will detrimentally etch the metal oxide.

The acid contacted metal oxide is then optionally rinsed, preferably with water. Rinsing of the acid contacted metal oxide does not reduce the enhanced adsorptive capability of the particle. When rinsed, the metal oxide is preferably rinsed with distilled water to minimize impurity contact. Rinsing of the metal oxide serves two purposes. First, any residual acid that is remaining on the surface or pores of the metal oxide is removed, which will make the metal oxide easier to handle when it is in the dry form. Second, rinsing the metal oxide will remove the counter-ion of the acid that may be on the surface or pores of the metal oxide.

Optionally, the acid treated metal oxide is dried by a low to moderate heat treatment to remove excess liquid, such as acid or water, from the rinsing. Typically, the drying is from about 50° C. to about 200° C. Drying of the metal oxide also reduces the transfer cost of the particle. However, the acid treated metal oxide is preferably not calcined or recalcined after acid treatment. Such recalcining would detrimentally change the surface characteristics by closing up the micropores. Additionally, the acid treated metal oxide used in the invention is preferably not sintered, either before or after the acid treatment step, as this would detrimentally affect the micropores by closing up the micropores and would detrimentally decrease the pore volume and surface area. Any other process, such as a heat treatment, that would increase the size or eliminate micropores, enlarge the size of, create or destroy macropores, or would decrease the surface area should preferably be avoided, particularly, after the metal oxide is acid treated.

In one embodiment, prior to admixing the support with the first biocidal compound, the support is a metal oxide that is (1) calcined at a particle temperature of from 200 to 700° C., and (2) contacted with a dilute acid, wherein the acid contacting is more than a surface wash but less than an etching, wherein the resultant acid treated metal oxide is not subsequently calcined. Preferably, the acid treated metal oxide is aluminum oxide.

Biocidal compounds useful in the present invention include, but are not limited to an elemental metal, a metal salt, or a combination thereof. The phrase "biocidal compound" as used herein is any compound that kills a bioactive agent present in the environment or renders the bioactive agent inactive. "Biocidal compound" also refers to any compound that can prevent the growth of new bioactive agents. Therefore, the biocidal compounds used in the present invention are also biostatic in nature.

In one embodiment, the biocidal compound comprises a metal salt. In one embodiment, the biocidal compound is partially soluble to completely soluble in a solvent, wherein the solvent is preferably water. Examples of biocidal compounds useful in the present invention include, but are not limited to, a zinc compound, a mercury compound, a lead compound, an iron compound, a cobalt compound, a nickel compound, a manganese compound, an arsenic compound, an antimony compound, a bismuth compound, a cadmium compound, a chromium compound, or a combination thereof. In a preferred embodiment, the biocidal compound comprises a silver compound, a copper compound, or a combination thereof.

Examples of silver compounds include, but are not limited to, $AgNO_3$, $Ag_2CO_3$, AgOAc, $Ag_2SO_4$, $Ag_2O$, AgCl, AgBr, AgI, silver acetoacetate, a silver benzoate, a silver carboxylate, or a combination thereof. Examples of copper compounds include, but are not limited to $Cu(NO_3)_2$, $Cu(NO_3)_2.2.5\ H_2O$, $CuCO_3$, $CuSO_4$, $CUCl_2$, $CuBr_2$, $CuI_2$, CuO, $Cu_2O$, CuI, $Cu(OAc)_2$, copper acetoacetate, copper gluconate, a copper benzoate, a copper carboxylate, or a combination thereof.

With respect to groups VI–X, the invention contemplates the use of any prior art adsorbent and/or catalyst compound or composite composition of two or more types of adsorbent and/or catalyst compounds as the first adsorbent and/or catalyst compound. In a preferred embodiment, the first adsorbent and/or catalyst compound comprises an oxide compound. The compound in one embodiment comprises a metal or metalloid oxide particle. Examples of such compounds include, but are not limited to, oxide complexes, such as transition metal oxides, lanthanide oxides, thorium oxide, as well as oxides of Group IIA (Mg, Ca, Sr, Ba), Group IIIA (B, Al, Ga, In, Tl), Group IVA (Si, Ge, Sn, Pb), and Group VA (As, Sb, Bi). In another embodiment, the compound comprises an oxide of aluminum, titanium, copper, vanadium, silicon, manganese, iron, zinc, zirconium, tungsten, rhenium, arsenic, magnesium, thorium, silver, cadmium, tin, lead, antimony, ruthenium, osmium, cobalt or nickel or zeolite. Typically, any oxidation state of the oxide complexes may be useful for the present invention. The oxide can be a mixture of at least two metal oxide compounds having the same metal with varying stoichiometry and oxidation states. In one embodiment, the adsorbent and/or catalyst compound comprises $Al_2O_3$, $TiO_2$, CuO, $Cu_2O$, $V_2O_5$, $SiO_2$, $MnO_2$, $Mn_2O_3$, $Mn_3O_4$, ZnO, $WO_2$, $WO_3$, $Re_2O_7$, $As_2O_3$, $As_2O_5$, MgO, $ThO_2$, $Ag_2O$, AgO, CdO, $SnO_2$, PbO, FeO, $Fe_2O_3$, $Fe_3O_4$, $Ru_2O_3$, RuO, $OsO_4$, $Sb_2O_3$, CoO, $Co_2O_3$, NiO or zeolite. In another embodiment, any of the biocidal compounds described above can be used as the first adsorbent and/or catalyst compound.

In a further embodiment, the first adsorbent and/or catalyst compound further comprises a second type of adsorbent and/or catalyst compound of an oxide of aluminum, titanium, copper, vanadium, silicon, manganese, iron, zinc, zirconium, tungsten, rhenium, arsenic, magnesium, thorium, silver, cadmium, tin, lead, antimony, ruthenium, osmium, cobalt or nickel or zeolite, activated carbon, including coal and coconut carbon, peat, zinc or tin. In another embodiment, the first adsorbent and/or catalyst compound further comprises a second type of adsorbent and/or catalyst compound of aluminum oxide, titanium dioxide, copper oxide, vanadium pentoxide, silicon dioxide, manganese dioxide, iron oxide, zinc oxide, zeolite, activated carbon, peat, zinc or tin particle. Typical zeolites used in the present invention include "Y" type, "beta " type, mordenite, and ZsM5. In one embodiment, the first adsorbent and/or catalyst compound comprises aluminum oxide that was produced by calcining the precursor to the calcined aluminum oxide at a particle temperature of from 400° C. to 700° C.

The precursor to calcined aluminum oxide can include but is not limited to boehmite, bauxite, pseudo-boehmite, scale, Al(OH)$_3$ and alumina hydrates. In the case of other metal oxide complexes, these complexes can also be calcined or uncalcined.

In one embodiment, when the support is a metal oxide, the first adsorbent and/or catalyst compound and the metal oxide are not the same compound. In another embodiment, when the support is a metal oxide, the metal oxide and the first adsorbent and/or catalyst compound are the same compound. For example, the metal oxide support can be calcined or sintered aluminum oxide, and the first adsorbent and/or catalyst particle can be acid treated aluminum oxide that has not been calcined or sintered.

The support and the (a) first biocidal compound or (b) first adsorbent and/or catalyst compound can be admixed using a variety of techniques known in the art. In one embodiment, when the support comprises a metal oxide, and the first biocidal compound or the first adsorbent and/or catalyst compound comprises a metal oxide or an elemental metal, then an acidic solvent is used to admix the components. In another embodiment, the support and the first biocidal compound or first adsorbent and/or catalyst compound are admixed in the presence of a solvent. Many solvents can be used to admix the support and the first biocidal compound or the first adsorbent and/or catalyst compound. In one embodiment, the solvent used to admix the support and the first biocidal compound or the first adsorbent and/or catalyst compound comprises water, acidic water, basic water, an alcohol, a ketone, an ester, an ether, an aldehyde, a polyol, or a combination thereof. Alternatively, the support and the first biocidal compound or the first adsorbent and/or catalyst compound can be admixed in dry form, and the dry mixture is optionally contacted with a solvent. In another embodiment, the admixing step comprises metathesizing the first biocidal compound on the support. The metathesis of biocidal compounds onto a support is well known in the art. In a preferred embodiment, the admixing step comprises mixing the support with first biocidal compound/solvent system. In this embodiment, the first biocidal compound is partially soluble or completely soluble in the solvent, preferably water, prior to contacting the support with the first biocidal compound/solvent system.

After the admixing step, the mixture is composed of an intimate mixture of the support and the first biocidal compound or the first adsorbent and/or catalyst compound. It is advantageous to intimately admix the support and the first biocidal compound or the first adsorbent and/or catalyst compound so that the first biocidal compound or the first adsorbent and/or catalyst compound is incorporated deep within the pores of the support.

In one embodiment, once the support and the first biocidal compound or the first adsorbent and/or catalyst have been admixed, the resultant composition is heated from 80 to 1,800° C. The lower limit of the heating temperature is 80, 100, 150, 200, 250, 300, 350, 400, 450, 500, 600, 700, 800, 900, or 1,000° C., and the upper limit of the heating temperature is 700, 750, 800, 850, 900, 950, 1,000, 1,100, 1,200, 1,300, 1,400, 1,500, 1,600, or 1,700° C. Generally, after the heating step, the composition is allowed to cool to room temperature prior to conducting any additional steps (e.g., reduction step). In one embodiment, when the support is a metal oxide, by varying the heating temperature, it is possible to adjust or modify the phase, the number of Lewis or Bronsted sites, the surface area, and the pore volume of the metal oxide, which ultimately can be used to control the rate of release of the first biocidal compound from the metal oxide support.

In one embodiment, once the support and the first biocidal compound or the first adsorbent and/or catalyst compound have been admixed, the resultant composition is dried from 20 to 50° C., preferably at 20 to 30° C., more preferably at 25° C. in order to remove any residual solvent that may be present in the admixture. Generally, the drying step is performed by allowing the composition to stand at ambient temperature for a sufficient time so that the majority of the solvent has evaporated. The dried mixture then can either be contacted with the reducing agent, or the dried mixture can be heated at from 80 to 1,800° C. then subsequently contacted with the reducing agent. In a preferred embodiment, when the dried mixture is composed of an aluminum oxide support and the biocidal compound is a silver compound, the dried mixture is contacted with a reducing agent.

The amount of first biocidal compound or the first adsorbent and/or catalyst compound that can be admixed with the support can vary depending upon the first biocidal compound, the first adsorbent and/or catalyst compound, and the support that are selected and the application of the resulting composition. In one embodiment, the support is from 0.1 to 99.9% by weight and the first biocidal compound or the first adsorbent and/or catalyst compound is from 0.1 to 99.9% by weight, wherein the sum of the first biocidal compound or the first adsorbent and/or catalyst compound and the support is 100%. In another embodiment, the support is from 5 to 95%, 10 to 90%, 20 to 80%, or 30 to 70% by weight, and the first biocidal compound or the first adsorbent and/or catalyst compound is from 5 to 95%, 10 to 90%, 20 to 80%, or 30 to 70% by weight, wherein the sum of the first biocidal compound or the first adsorbent and/or catalyst compound and the support is 100%. Although the sum of the support and the first biocidal compound or the first adsorbent and/or catalyst compound is 100%, the composition can include other components, such as additives and fillers.

In one embodiment, any of the compositions of the present invention can be contacted with a reducing agent to reduce at least some of the first biocidal compound or the first adsorbent and/or catalyst compound present in the composition. The phrase "at least some" when referring to the amount of first biocidal compound or the first adsorbent and/or catalyst compound that is reduced or oxidized is defined as greater than 0% to a maximum of 100% reduction or oxidation of the first biocidal compound or the first adsorbent and/or catalyst compound. In various embodiment, the lower limit of reduction or oxidation is 1, 5, 10, 15, 20, 25, 30, 35, 40, 50, 60, 70, or 80% and the upper limit 20, 25, 30, 35, 40, 50, 60, 70, 80, 90, 95, or 100%. Additionally, the support may also be reduced depending upon the type of support and reducing agent that is used.

In one embodiment, when the first biocidal compound is a metal salt, the metal ion can either be fully reduced to the corresponding elemental metal or it can be reduced to a metal ion having a lower oxidation state. In a preferred embodiment, when the first biocidal compound is a metal salt, the metal salt is reduced to elemental metal. One advantage of the reduction step is that by reducing the first biocidal compound, the rate of release of the first biocidal compound from the support can be controlled. Additionally, the reduction step results in the formation of a reduced composition having the first biocidal compound or the first adsorbent and/or catalyst compound in the form of elemental metal that is dispersed throughout support, which is capable of being oxidized to the corresponding metal oxide. By incorporating elemental metal within the support, the reduced compositions of the present invention can remove a bioactive agent from the environment via a number of different mechanisms when compared to prior art compositions that do not have an elemental metal incorporated throughout the support.

The majority of reducing agents known in the art can be used in the present invention. The selection of the reducing agent varies depending upon the redox potential of the first biocidal compound or the first adsorbent and/or catalyst compound and support that are used. For example, when the support is a metal oxide, it is possible to selectively reduce the first biocidal compound without reducing the metal oxide by knowing the reduction potential of the metal oxide and the first biocidal compound and the redox potential of the reducing agent. In one embodiment, the reducing agent comprises a reducing sugar or an antioxidant. Any reducing sugar known in the art can be used in the present invention as a reducing agent. Examples of reducing agents include, but are not limited to, glucose, fructose, formaldehyde, hydrazine, sodium dithionate, sodium bisulfite, ascorbic acid (vitamin C), or vitamin E. In another embodiment, when the biocidal compound is a silver compound, the reducing agent is ascorbic acid.

In another embodiment, any of the compositions of the present invention that contain at least some first reduced biocidal compound or at least some first reduced adsorbent and/or catalyst compound can be oxidized so that at least some of the first reduced biocidal compound or at least some of the first reduced adsorbent and/or catalyst compound is oxidized. When the first reduced biocidal compound or the first reduced adsorbent and/or catalyst compound is oxidized, it can be oxidized to a variety of oxidation states. The selection of the particular oxidizing agent depends upon the first reduced biocidal compound, the first reduced adsorbent and/or catalyst compound, and the support. By using redox potentials as described above, it is possible to selectively oxidize at least some of the first biocidal compound or the first adsorbent and/or catalyst compound and not the support. Additionally, some of the support can be oxidized as well. An advantage of the oxidation step is that when the first reduced biocidal compound or the first reduced adsorbent and/or catalyst compound is an elemental metal that is incorporated throughout the support, and the elemental metal is oxidized to the corresponding metal oxide, the resultant oxidized composition has colloidal metal oxide incorporated or impregnated throughout the support. Another advantage of the oxidation step is that it is possible to produce a composition that has elemental metal and the corresponding metal oxide dispersed throughout the support, which is difficult to reproduce using prior art techniques.

The majority of oxidizing agents known in the art can be used in the present invention. Examples of oxidizing agents include, but are not limited to, oxygen, ozone, hydrogen peroxide, $ClO_2$, $ClO_3^-$, air, or a combination thereof.

In another embodiment, the composition containing at least some first reduced biocidal compound or first reduced adsorbent and/or catalyst compound can be heated in air at from 80 to 1,500° C. in order to oxidize at least some of the first reduced biocidal compound or the first reduced adsorbent and/or catalyst compound. The lower limit of the heating temperature is 80, 100, 150, 20, 250, 300, 350, 400, 450, 500, 600, 700, 800, 900° C., and the upper limit is 500, 550, 600, 650, 700, 750, 800, 850, 900, 950, 1,000, 1,100, 1,200, 1,300, 1,400, or 1,500° C.

Any of the compositions of the present invention containing the first biocidal compound or the first adsorbent and/or catalyst compound can be contacted with the reducing agent or oxidizing agent using techniques known in the art. In one embodiment, the composition containing the support and the first biocidal compound or the first adsorbent and/or catalyst compound is contacted with an aqueous solution of the reducing agent or the oxidizing agent. The amount of reducing agent or oxidizing agent that is used can vary, and will depend on the amount of first biocidal compound or the first adsorbent and/or catalyst compound that is present in the composition as well as the desired degree of reduction or oxidation of the first biocidal compound or the first adsorbent and/or catalyst compound. In one embodiment, once the composition containing the first biocidal compound or the first adsorbent and/or catalyst compound has been contacted with the reducing agent, the resultant, reduced composition is contacted with an oxidizing agent. In one embodiment, the composition can be contacted with a reducing agent or oxidizing agent at from 0 to 100 ° C. In one embodiment, the mixing time can be as short as the time it takes the reducing or oxidizing agent to contact the composition up to an upper limit of 3 hours.

In one embodiment, (a) the support comprises an oxide of aluminum, titanium, copper, vanadium, silicon, manganese, iron, zinc, zirconium, magnesium, thorium, or a combination thereof; (b) the biocidal compound comprises a zinc compound, a mercury compound, a lead compound, an iron compound, a cobalt compound, a nickel compound, a manganese compound, an arsenic compound, an antimony compound, a bismuth compound, a cadmium compound, a chromium compound, a silver compound, a copper compound, or a combination thereof; and (c) the reducing agent comprises glucose, fructose, formaldehyde, hydrazine, sodium dithionate, sodium bisulfite, ascorbic acid, or a combination thereof.

In one embodiment, the support is aluminum oxide and the first biocidal compound is a silver compound, a copper compound, or a combination thereof In another embodiment, the support is aluminum oxide calcined at from 200 to 700° C. and the first biocidal compound is a silver compound, a copper compound, or a combination thereof.

In another embodiment, when the composition is a Group I composition, the support is aluminum oxide and the first biocidal compound is $AgNO_3$, wherein (1) the aluminum oxide and $AgNO_3$ are admixed then the mixture is heated from 100 to 600° C., and (2) the heated mixture is contacted with ascorbic acid. In another embodiment, when the composition is a Group I composition, the support is aluminum oxide and the first biocidal compound is $Cu(NO_3)_2 \cdot 2.5\ H_2O$, wherein (1) the aluminum oxide and $Cu(NO_3)_2 \cdot 2.5\ H_2O$ are admixed then the mixture is heated from 100 to 600° C.; and (2) the heated mixture is contacted with ascorbic acid. In another embodiment, when the composition is a Group I composition, the support is aluminum oxide and the first biocidal compound is $Cu(NO_3)_2 \cdot 2.5\ H_2O$, wherein (1) the aluminum oxide and $Cu(NO_3)_2 \cdot 2.5\ H_2O$ are admixed then the mixture is heated from 100 to 600° C.; and (2) the heated mixture is contacted with sodium dithionate.

In another embodiment, when the composition is a Group II composition, the support is aluminum oxide and the first biocidal compound is $Cu(NO_3)_2 \cdot 2.5\ H_2O$, wherein (1) the aluminum oxide and $Cu(NO_3)_2 \cdot 2.5\ H_2O$ are admixed then the mixture is heated at from 400 to 700° C., preferably 550° C.; (2) the heated mixture is contacted with $Na_2S_2O_4$; and (3) the reduced composition is heated in air at from 90 to 110° C.

In another embodiment, when the composition is a Group III composition, the support is aluminum oxide and the first biocidal compound is $AgNO_3$, wherein (1) the aluminum oxide and AgNO₃ are admixed then the mixture is dried at room temperature; and (2) the dried mixture is contacted with ascorbic acid.

The binders disclosed in international publication no. WO 97/47380 entitled "Acid Contacted Enhanced Adsorbent Particle and/or Catalyst and Binder System," which is herein incorporated by this reference in its entirety, are useful as the crosslinkable binders of the present invention.

The binder of the present invention comprises an oxide particle that is capable of reacting, preferably cross-linking, with (1) itself; (2) the support, and/or (3) the first biocidal compound or the first adsorbent and/or catalyst compound. In one embodiment, when the support is a metal oxide, the binder cross-links with the metal oxide upon drying by forming chemical bonds with itself and the metal oxide. Under acidic conditions, the binder has a large number of surface hydroxyl groups. In one embodiment, the binder, which is designated as B—OH, cross-links with itself upon the loss of water to generate B—O—B. In addition to cross-linking with itself, the binder B—OH can also cross-link with a metal oxide complex (M—O) or metal hydroxyl complex (M—OH) to produce B—O—M.

In another embodiment, when the support is a polymer, and the polymer possesses one or more hydroxyl groups, then the binder can cross-link with the polymer. In another embodiment, the hydroxyl groups present on the cellulosic fiber can also cross-link with the binder. The resulting binder/support system consists of a three dimensional network or matrix, wherein the first biocidal compound or the first adsorbent and/or catalyst compound is incorporated within the matrix or is cross-linked with the binder.

"Colloidal metal or metalloid oxide (i.e., colloidal metal oxide or colloidal metalloid oxide) binder" as defined herein means a particle comprising a metal or metalloid mixed hydroxide, hydroxide oxide, or oxide particle, such that the weight loss from the colloidal metal or metalloid oxide binder due to loss of water upon ignition is from 1 to 100%, 5 to 99%, 10 to 98%, or 50 to 95% of the theoretical water weight loss on going from the pure metal or metalloid hydroxide to the corresponding pure metal or metalloid oxide. The loss of water on going from the pure metal or metalloid hydroxide to the corresponding pure metal or metalloid oxide (e.g., the conversion of n $M(OH)_x$ to $M_nO_m$ and y $H_2O$ or more specifically from 2 $Al(OH)_3$ to $Al_2O_3$ and 3 $H_2O$) is defined as 100% of the water weight loss. Thus, the weight loss refers to loss of water based on the initial weight of water (not the total initial binder weight). There is a continuum of metal or metalloid hydroxides, hydroxide oxides, and oxides in a typical commercial product, such that, loss or removal of water from the metal or metalloid hydroxides produces the corresponding hydroxide oxides which upon further loss or removal of water give the corresponding metal or metalloid oxides. Through this continuum the loss or removal of water produces M—O—M bonds, where M is a metal or metalloid. The particles of this continuum, except for the pure metal or metalloid oxides, are suitable to serve as colloidal metal or colloidal oxide binders in this invention.

In another embodiment, the binder system involves the use of a binder in combination with a support and a first biocidal compound or the first adsorbent and/or catalyst compound with few or no surface hydroxyl groups, such that the support does not cross-link or only nominally cross-links with the binder. Examples of particles that posses only nominal amounts or that do not posses surface hydroxyl groups include particles of metals or non-metals, such as, but not limited to zinc or carbon, respectively. In this embodiment, the binder cross-links with itself in a manner described above to form a three dimensional network or matrix that physically entraps or holds the support and the first biocidal compound or the first adsorbent and/or catalyst compound without cross-linking or cross-linking only to a very small degree with the support.

Binders that can be used in the present invention are colloidal metal or metalloid oxide complexes. Colloidal as used herein is defined as an oxide group that has a substantial number of hydroxyl groups that can form a dispersion in aqueous media. This is to be distinguished from the other use of the term colloid as used in regard to a size of less than 1 $\mu$m. The binders herein are typically small in size, e.g. less than 150 $\mu$m, but they do not have to be all less than 1 $\mu$m. Typically, the binder is un-calcined to maximize the hydroxyl group availability. Moreover, they must have a substantial number of hydroxyl groups that can form a dispersion in aqueous media, which is not always true of colloid particles merely defined as being less than 1 $\mu$m. Examples of binders include but are not limited to any metal or metalloid oxide complex that has a substantial number of hydroxyl groups that can form a dispersion in aqueous media. In one embodiment, the binder is colloidal aluminum oxide, colloidal silicon dioxide, colloidal iron oxide, or a mixture thereof, preferably colloidal aluminum oxide or colloidal silicon dioxide. Colloidal aluminum oxide can be a powder, sol, gel or aqueous dispersion. Colloidal aluminum oxide may be further stabilized with an acid, preferably nitric acid, and even more preferably 3 to 4% nitric acid.

In one embodiment, the binder is from 1% to 99.9% by weight of the mixture, preferably from 10% to 35% by weight. As used herein, the binder will be referred to as "colloidal" to distinguish it from the metal oxides that can be used as the support material, as the composition types can be the same, e.g. both can contain aluminum oxides.

In a preferred embodiment, the colloidal aluminum oxide is un-calcined with a sufficient number of hydroxyl groups such that the total particle weight loss (as distinguished from just water weight loss discussed above) upon ignition is between from 5% to 34%, more preferably from 20% to 31). The colloidal aluminum oxide size is preferably from 5 nm to 400 $\mu$m, preferably at least 30 wt % is less than 25 $\mu$m and 95wt % is less than 100 $\mu$m.

In another embodiment, the colloidal silicon dioxide is un-calcined with a sufficient number of hydroxyl groups such that the total particle weight loss upon ignition is between from 5% to 37%, more preferably from 20% to 31%. The colloidal silicon dioxide size is preferably from 5 nm to 250 $\mu$m, preferably at least 30 wt % is less than 25 $\mu$m and 95 wt % is less than 100 $\mu$m.

An acid facilitates the cross-linking the binder with (1) itself; (2) the support; (3) and/or the first biocidal compound or the first adsorbent and/or catalyst compound. The addition of an acid to the binder facilitates or enables the reaction (i.e., cross-linking) between the binder with itself and the different components. A strong or dilute acid can be used. In one embodiment, the acid is diluted with water to prevent dissolution of the particle and for cost effectiveness. The acid treatment is preferably of a concentration (i.e. acid strength as measured by, e.g., normality or pH), acid type, temperature and length of time to cross-link the binder with itself, the support, and/or the first biocidal compound or the first adsorbent and/or catalyst compound.

In one embodiment, the acid comprises nitric acid, sulfuric acid, hydrochloric acid, boric acid, acetic acid, formic acid, phosphoric acid or mixtures thereof, preferably acetic acid or nitric acid. In another embodiment, the concentration of the acid is from 0.15 N to 8.5 N, preferably from 0.5 N to 1.7 N. The volume of dilute acid used must be high enough so that the compositions of the present invention can be used as is or further processed, such as extruded or filter pressed.

In order to ensure efficient cross-linking, water is preferably removed from the resulting binder/biocidal composition or the binder/adsorbent and/or catalyst composition. This is typically performed by using a drying agent or heating the system. The cross-linking temperature as used herein is the temperature at which the binder cross-links with itself, the support, and/or the first biocidal compound or the first adsorbent and/or catalyst compound at an acceptable rate. In one embodiment, the cross-linking temperature is from 25° C. to 400 ° C. Thus, in one embodiment, the cross-linking temperature for certain binders is at room temperature although the rate of cross-linking at this temperature is slow. In a various embodiments, the cross-linking temperature is from 50° C., 70° C., 110° C., or 150° C. to 200° C., 250° C., 300° C., or 350° C., preferably 150° C. to 300° C., even more preferably about 250° C. In one embodiment, when the binder is colloidal aluminum oxide or colloidal silicon dioxide, the cross-linking temperature is from 75° C. to 150° C. The cross-linking process can take place in open air, under an inert atmosphere or under reduced pressure.

In another embodiment, after the cross-linking step, the binder/biocidal composition or the binder/adsorbent and/or catalyst composition is heated from 80 to 1,800° C. in order to vary the surface area and pore volume of the composition. The lower limit of the heating temperature is 80, 100, 150, 20, 250, 300, 350, 400, 450, 500, 600, 700, 800, 900° C., and the upper limit is 500, 550, 600, 650, 700, 750, 800, 850, 900, 950, 1,000, 1,100, 1,200, 1,300, 1,400, 1,500, 1,600, 1,700, or 1,800° C. In one embodiment, by heating the binder/biocidal composition at different temperatures, it is possible to control the rate of release of the first biocidal composition from the binder/biocidal composition. In one embodiment, the binder/biocidal composition or the binder/adsorbent and/or catalyst composition is calcined. In another embodiment, the binder/biocidal composition or the binder/adsorbent and/or catalyst composition is sintered.

The binder/biocidal composition or the binder/adsorbent and/or catalyst composition of the present invention can be prepared by a variety of techniques. In one embodiment, the (1) binder; (2) the support; and (3) the first biocidal compound or the first adsorbent and/or catalyst particle are pre-mixed in dry form. The colloidal binder can be added or prepared in situ. For example, alum could be added as a dry powder and converted to colloidal aluminum oxide in situ. Other aluminum based compounds can be used for the in situ process, such as aluminum chloride, aluminum secondary butoxide, and the like. A solution of the acid is added to the mixture, and the mixture is stirred or agitated, typically from 1 minute to 2 hours, preferably from 10 minutes to 40 minutes, until the material has a homogeneous "clay" like texture. The mixture is then ready for cross-linking or can be first fed through an extruder and then cut or chopped into a final shape. After the final shape is made, the mixture is transferred to a drying oven where it is dried from 15 minutes to 4 hours, preferably from 30 minutes to 2 hours. In another embodiment, the binder and support is admixed with an acid and the resultant mixture is crosslinked to produce a binder/support system, then the binder/support system is subsequently admixed with the first biocidal compound or the first adsorbent and/or catalyst compound.

Any support described above can be used in combination with the binder and the first biocidal compound or the first adsorbent and/or catalyst compound. In one embodiment, the support comprises aluminum oxide, silicon dioxide, or an oxide of magnesium, preferably aluminum oxide. In another embodiment, when the support is a metal oxide, the metal oxide is (1) calcined at a particle temperature of from 200 to 700° C., and (2) contacted with a dilute acid, wherein the acid contacting is more than a surface wash but less than an etching, wherein the resultant acid treated metal oxide is not subsequently calcined. In a preferred embodiment, the acid treated metal oxide is aluminum oxide.

Any of the biocidal compounds or adsorbent and/or catalyst compounds previously disclosed can be used to prepare the binder/biocidal composition or the binder/adsorbent and/or catalyst composition, respectively. In a preferred embodiment, the first biocidal compound comprises a silver compound, a copper compound, or a combination thereof.

In one embodiment, a binder of the present invention can be combined with compositions I, II, III, VI, VII, and/or VIII to produce a binder/biocidal composition or a binder/adsorbent and/or catalyst composition. In one embodiment, composition I, II, III, VI, VII, and/or VIII can be (i) admixed with a binder comprising a colloidal metal oxide or colloidal metalloid oxide and an acid to produce a mixture, and (ii) removing a sufficient amount of water from the mixture to cross-link the binder with itself and/or the composition to produce a binder/biocidal composition or a binder/adsorbent and/or catalyst composition.

In one embodiment, once the binder/biocidal composition or the binder/adsorbent and/or catalyst composition is produced, it can be contacted with a (1) reducing agent; or (2) a reducing agent followed by an oxidizing agent using the techniques and reagents described above. Alternatively, after the binder/biocidal composition or the binder/adsorbent and/or catalyst composition has been contacted with a reducing agent, the reduced composition can be heated in air at from 80 to 120° C. in order to oxidize at least some of the first reduced biocidal compound or the first reduced adsorbent and/or catalyst compound.

In one embodiment, the binder is colloidal aluminum oxide, the support is aluminum oxide, and the first biocidal compound is a copper compound, a silver compound, or combination thereof. In another embodiment, the binder is colloidal aluminum oxide, the support is aluminum oxide, and the first biocidal compound is a copper compound, wherein the resultant mixture is contacted with a reducing agent to reduce at least some of the first biocidal composition to produce a reduced mixture, and oxidizing at least some of the first biocidal compound in the reduced mixture.

Any of the compositions of the present invention can be admixed with a second biocidal compound or second adsorbent and/or catalyst compound to produce a new composition containing a first and second biocidal compound or adsorbent and/or catalyst compound. The second biocidal compound can be any of the first biocidal compounds previously disclosed. In a preferred embodiment, the second biocidal compound is a silver compound, a copper compound, or a combination thereof. Additionally, the second adsorbent and/or catalyst compound can be any of the first adsorbent and/or catalyst compounds described above. Once the composition containing the first and second biocidal compound or the first and second adsorbent and/or catalyst compound has been produced, the resultant composition can be contacted with (1) a reducing agent to reduce at least some of the second biocidal compound or at least some of the second adsorbent and/or catalyst compound; or (2) a reducing agent to reduce at least some of the second biocidal compound or at least some of the second adsorbent and/or catalyst compound followed by oxidizing at least some of the second reduced biocidal compound or at least some of the second reduced adsorbent and/or catalyst compound.

In one embodiment, the binder/biocidal composition can be admixed with a second biocidal compound to produce a second binder/biocidal composition, followed by contacting the second binder/biocidal composition with (1) a reducing agent to reduce at least some of the second biocidal compound; or (2) a reducing agent to reduce at least some of the second biocidal compound followed by oxidizing at least some of the second reduced biocidal compound. Alternatively, the binder/biocidal composition is (I) contacted with (1) a reducing agent to reduce at least some of the first biocidal compound; or (2) a reducing agent to reduce at least some of the first biocidal compound followed by oxidizing at least some of the first biocidal compound to produce a reduced and/or oxidized binder/biocidal composition, and (II) admixing a second biocidal compound with the reduced and/or oxidized binder/biocidal composition.

In one embodiment, the binder/adsorbent and/or catalyst composition can be admixed with a second adsorbent and/or catalyst compound to produce a second binder/adsorbent and/or catalyst composition, followed by contacting the second binder/adsorbent and/or catalyst composition with (1) a reducing agent to reduce at least some of the second adsorbent and/or catalyst compound; or (2) a reducing agent to reduce at least some of the second adsorbent and/or catalyst compound followed by oxidizing at least some of the second reduced adsorbent and/or catalyst compound. Alternatively, the binder/adsorbent and/or catalyst composition is (I) contacted with (1) a reducing agent to reduce at least some of the first adsorbent and/or catalyst compound; or (2) a reducing agent to reduce at least some of the first adsorbent and/or catalyst compound followed by oxidizing at least some of the first adsorbent and/or catalyst compound to produce a reduced and/or oxidized binder/adsorbent and/or catalyst composition, and (II) admixing a second adsorbent and/or catalyst compound with the reduced and/or oxidized binder/adsorbent and/or catalyst composition.

The size and shape of the particles present in the composition can vary greatly depending on the end use. In one embodiment, the compositions of the present invention can be extruded to a particular shape and size using techniques known in the art. In one embodiment, when the composition is used to remove a bioactive agent or contaminant from a liquid, the particle size is from 5 $\mu$m to 4 mm, preferably 50 $\mu$m to 1.5 mm. In another embodiment, when the composition is used to remove a bioactive agent or contaminant from a gas, the particle size is from 5 $\mu$m to 4 mm, preferably 100$\mu$m to 2 mm.

In yet another aspect, the invention provides a method for reducing or eliminating the amount of a bioactive agent from an environment, comprising contacting the environment with a composition containing a biocidal compound for a sufficient time to reduce or eliminate the amount of the bioactive agent in the environment.

The invention further relates to a method for reducing or eliminating the amount of a contaminant from an environment, comprising contacting the environment with a composition containing an adsorbent and/or catalyst compound for a sufficient time to reduce or eliminate the amount of the contaminant in the environment. In one embodiment, contaminants in an environment can be reduced or eliminated by a catalysis reaction. In another embodiment, contaminants in an environment can be reduced or eliminated by an adsorption reaction.

Any environment containing a bioactive agent or contaminant can be contacted with a composition of the present invention in order to reduce or eliminate the amount of the bioactive agent or contaminant in the environment. The term "environment" as used herein refers to any media that contains at least one bioactive agent or at least one contaminant. In one embodiment, the environment is a liquid, preferably water. In another embodiment, the environment is a gas, preferably air.

The term "reduce" herein refers to decreasing the amount of the bioactive agent or contaminant present in the environment when compared to the amount of the bioactive agent or contaminant present in the environment prior to contacting the environment with the composition. The term "reduce" can also refer to the reduction of the rate of growth of new bioactive agent in the environment over time (i.e., biostatic). The term "reduce" can also refer to the injuring the bioactive agent so that the rate of reproduction of the bioactive agent is reduced. The term "eliminate" herein refers to the removal of the majority of the bioactive agent or the contaminant from the environment (i.e., biocidal).

The phrase "bioactive agent" generally refers to any microorganism known in the art that may be present in the environment. Examples of bioactive agents include, but are not limited to, gram-positive bacteria, gram-negative bacteria, yeast, mold, protozoa, viruses, or a combination thereof.

The compositions can be used to remove contaminants, such as, but not limited to, heavy metals, organics, including hydrocarbons, chlorinated organics, including chlorinated hydrocarbons, inorganics, or mixtures thereof. Specific examples of contaminants include, but are not limited to, acetone, ammonia, benzene, carbon monoxide, chlorine, hydrogen sulfide, trichloroethylene, 1,4-dioxane, ethanol, ethylene, formaldehyde, hydrogen cyanide, methanol, methyl ethyl ketone, methylene chloride, oxides of nitrogen such as nitrogen oxide, propylene, styrene, oxides of sulfur such as sulfur dioxide, toluene, vinyl chloride, arsenic, cadmium, chlorine, 1,2-dibromochloropropane (DBCP), iron, lead, phosphate, radon, selenium, an anion, an oxoanion, a poly-oxoanion or an uranium compound, such as $U_3O_8$. The compositions of this invention can remediate individual contaminants or multiple contaminants from a single source. In a preferred embodiment, the contaminant that is removed from the environment is hydrogen sulfide or sulfur dioxide.

The compositions of the present invention can be used for a variety of applications. When the environment is a liquid media, the composition of the invention is typically placed in a container, such as a cartridge. The contaminated liquid enters the container at one end, contacts the composition within the container, and the purified liquid exits through another end of the container. The compositions can be used in dry form or can be prepared as a slurry. In one embodiment, the compositions of the present invention can be used to remove or eliminate a bioactive agent from drinking water. In another embodiment, the compositions of the present invention can be used to produce sterilized water that is used to reconstitiute blood.

In one embodiment, the environment can be a gas stream, wherein the gas stream is allowed to pass through a device containing a composition of the present invention. For example, the compositions of the present invention can be used as air filters. In another embodiment, the compositions of the present invention can be used to remove a bioactive agent or contaminant from air, where the air is not a gas stream. For example, when the support is a cellulosic fiber, such as wallpaper or wood, the composition can reduce or eliminate the amount of the bioactive agent or contaminant when the bioactive agent or contaminant contacts the wallpaper or wood.

Not wishing to be bound by theory, it is believed that bioactive agent absorbs and/or adsorbs onto the biocidal composition, which results in the death of the bioactive agent. It is also believed that the bioactive agent can induce the release of some of the biocidal compound from the composition. The release of the biocidal compound can kill the bioactive agent present in the environment, as well as prevent the growth of new bioactive agents. Additionally, the support over time can leach out the biocidal compound. The amount of biocidal compound that is released into the environment can vary depending upon the support system and biocidal compound that are selected, the bioactive agent present in the environment, and the method used to prepare the biocidal composition. Finally, as described above, the incorporation of elemental metal within the support using the process of the present invention results in the reduction or elimination of the bioactive agent in an environment via a number of different biological mechanisms.

In another embodiment, the invention relates to a method for reducing or eliminating the amount of a bioactive agent from an environment, comprising contacting the environment with a biocidal compound system, wherein the biocidal compound system comprises:

(a) a first layer comprising a scavenger, wherein the first layer has a first surface and a second surface, and (b) a second layer comprising a biocidal composition of the present invention, wherein the second layer has a first surface and a second surface, wherein the first surface of the first layer is adjacent to and in contact with the first surface of the second layer, for a sufficient time to reduce or eliminate the amount of the bioactive agent in the environment.

The invention further relates to a method for reducing or eliminating the amount of a bioactive agent from an environment, comprising contacting the environment with a biocidal compound system, wherein the biocidal compound system comprises:

(a) a first layer comprising the composition produced by the process comprising:

(i) admixing a first support with a first biocidal compound to produce a mixture;

(ii) heating the mixture produced in step (i) at from 80 to 1,800° C. to produce a heated mixture;

(iii) contacting the heated mixture produced in step (ii) with a reducing agent to reduce at least some of the first biocidal compound to produce a first reduced biocidal/support composition; and (iv) oxidizing at least some of the first biocidal compound in the first reduced biocidal/support composition to produce a first oxidized biocidal/support composition, wherein the first layer has a first surface and a second surface, and (b) a second layer comprising the composition produced by the process comprising:

(v) admixing a second support with a second biocidal compound to produce a mixture;

(vi) heating the mixture produced in step (v) at from 80 to 1,800° C. to produce a heated mixture; and (vii) contacting the heated mixture produced in step (vii) with a reducing agent to reduce at least some of the second biocidal compound to produce a second reduced biocidal/support composition, wherein the first surface of the first layer is adjacent to and in contact with the first surface of the second layer, for a sufficient time to reduce or eliminate the amount of the bioactive agent in the environment.

The invention further relates to a method for reducing or eliminating the amount of a bioactive agent from an environment, comprising contacting the environment with a biocidal compound system, wherein the biocidal compound system comprises:

(I) a first layer comprising a binder composition, wherein the binder composition is produced by the method comprising (i) mixing components comprising
(a) a binder comprising a colloidal metal oxide or colloidal metalloid oxide,
(b) an oxide adsorbent and/or catalyst particle, and
(c) an acid, and (ii) removing a sufficient amount of water from the mixture to cross-link the binder with itself and/or component b to form a binder composition, wherein the first layer has a first surface and a second surface, and (II) a second layer comprising the composition produced by the process of the present invention, wherein the second layer has a first surface and a second surface, wherein the first surface of the first layer is adjacent to and in contact with the first surface of the second layer, for a sufficient time to reduce or eliminate the amount of the bioactive agent in the environment.

The term "adjacent" means that the layers in the multi-layered structure are in close proximity to one another, and may or may not imply that the layers are in direct contact with one another.

The term "contact" means that the layers in the multi-layered structure are touching one another, and are not separated by an intermediate layer(s).

Generally, the biocidal compound system is held in a column. Any column known in the art can be used to hold the biocidal compound system, and the size and shape of the column that is selected will vary depending upon the application. In one embodiment, as the environment enters the column and passes through the biocidal composition, the amount of the bioactive agent is reduced or eliminated from the environment. The environment then passes through the scavenger. The role of the scavenger is to remove any biocidal compounds that may have leached out of the biocidal composition and entered into the environment. Additionally, the scavenger can remove trace amounts of metals and other contaminants that may be present in the environment. In one embodiment, the scavenger is a metal oxide, an ion exchange polymer or resin, or a zeolite. In a preferred embodiment, the scavenger is aluminum oxide. After the environment has passed through the scavenger, the purified environment exits the column. In one embodiment, this application can be used to remove a bioactive agent from drinking water.

Any of the biocidal compositions of the present invention containing a first biocidal compound can be used in the second layer of the biocidal compound system. In one embodiment, the biocidal composition forms a layer that is applied on top of the scavenger. In one embodiment, the second layer comprises a Group I composition. In a preferred embodiment, the second layer is a Group I composition having a silver compound. Alternatively, two or more different biocidal compositions of the present invention can be admixed to produce a new biocidal composition, and the new biocidal composition can be placed on top of the scavenger in order to form the second layer.

In another embodiment, two or more layers of biocidal compositions can be used in the biocidal compound system. In one embodiment, the biocidal compound system having a second layer, further comprises a third layer comprising a biocidal composition, wherein the third layer has a first surface and a second surface, wherein the first surface of the third layer is adjacent to and in contact with the second surface of the second layer. In one embodiment, the biocidal composition in the second layer is different than the composition in the third layer. In another embodiment, the second layer and the third layer can contain the same biocidal compound. For example, the biocidal compound in the second layer may be a copper compound that has been reduced, while the copper compound in the third layer may have been reduced and subsequently oxidized. In one embodiment, the biocidal compound composition comprises (1) a second layer composed of a group I composition, where the biocidal compound is a silver compound, and (2) a third layer comprising a Group II composition, where the biocidal compound is a copper compound.

In one embodiment, when the biocidal compound system is composed of two layers, the first layer is composed of a Group II composition, wherein the first support is aluminum oxide and the first biocidal compound is a copper compound; and the second layer is composed of a Group I composition, wherein the second support is aluminum oxide and the second biocidal compound is a silver compound.

In one embodiment, when the environment is passed through the biocidal compound system, it initially contacts the second surface of the second layer. In this embodiment, the term "initially" refers to the environment contacting the second surface of the second layer first before contacting the first layer. In another embodiment, the environment initially contacts the second surface of the third layer. In this embodiment, the environment first contacts the third layer, then the second layer, then finally the first layer.

In one embodiment, prior to contacting the biocidal compound system with the environment, the biocidal compound system is flushed with water, a dilute acid, or a dilute base.

In another embodiment, a binder composition can be used in combination with any of the compositions of the present invention to produce the biocidal compound system. The binder composition can be any binder system disclosed in international publication no. WO 97/47380. In one embodiment, (1) the first layer comprises a binder composition prepared by admixing manganese dioxide, aluminum dioxide, aluminum oxide, and colloidal aluminum oxide; and (2) the second layer comprises aluminum oxide that has been impregnated with a silver compound; heated at from 80 to 1,800° C.; then contacted with a reducing agent.

Although the adsorbent and/or catalyst compositions of the present invention can bond tightly to the contaminant, the composition can be regenerated by various techniques. In one embodiment, the composition can be regenerated by roasting it in air to reoxidize the composition. In another embodiment, the contaminant can be removed by contacting the composition having the adsorbed contaminant with a reagent wash. The reagent wash can include but is not limited to aqueous ammonia, phosphines or detergents. In yet another embodiment, the use of a pH swing can remove the contaminant from the composition. Various pH ranges can be used to remove the contaminant from the composition depending upon the type of contaminant. In another embodiment, Lewis acids and bases can be used to remove the contaminant from the composition.

In another embodiment, the biocidal compositions can be regenerated by washing the biocidal composition with reagents known in the art that can remove or strip off the dead or trapped bioactive agent from the composition.

Experimental

The following examples are put forth so as to provide those of ordinary skill in the art with a complete disclosure and description of how the compositions claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature and pressure is at or near atmospheric.

Example 1

Silver Impregnation: Aluminum oxide (Alcan AA300 green bodies sized to 212–300 μm, 30 mL) was treated with 15 mL of an aqueous $AgNO_3$ solution, which contains an amount of $AgNO_3$ equivalent to 1% of the weight of the aluminum oxide. The aluminum oxide and aqueous $AgNO_3$ were mixed with a spatula in a 50 mL beaker until all of the aluminum oxide was covered with the liquid. The composition was allowed to dry at room temperature over night. The composition was then calcined as indicated in Table 1.

Reduction of silver/aluminum oxide composition: The silver/aluminum oxide compositions produced above were each treated with the reducing agent ascorbic acid (Vitamin C). The compositions were independently added to a solution of ascorbic acid with stirring in a ratio of 0.112 g of ascorbic acid in 80 mL of water for each 20 g of composition. The mixture was stirred for 5 minutes, then the reduced composition was allowed to stand at room temperature for one hour. The liquid was decanted, and the reduced composition was then washed twice with 100 mL portions of deionized $H_2O$.

Leachability Study: The reduced compositions, approximately 20 mL, were separately transferred to a column fitted with a stopcock. A solution of $Ca^{2+}$ was prepared by dissolving 0.555 g of $CaCl_2$ in 10 L of $H_2O$ to make a solution 20 ppm in $Ca^{2+}$. The $Ca^{2+}$ solution was allowed to flow through each reduced composition at approximately 10 mL/min ( 1/2 bed volume/min). A 10 mL sample was collected at pre-selected eluted bed volumes as indicated in Table 1. One drop of concentrated $HNO_3$ was added to each sample as a preservative. These samples were analyzed by ICP/MS. Table 1 gives the concentration of silver in the effluent in ppb as a function calcining time, temperature, and bed volume eluted.

TABLE 1

Calcining Time and Temperature for Biocidal Media Preparation and Leaching Study for Silver and Aluminum.

| Calcining Temp. (time) | 100° C. (1 Hr) | 250° C. (1 Hr) | 350° C. (1 Hr) | 450° C. (1 Hr) | 550° C. (1 Hr) | |
|---|---|---|---|---|---|---|
| Bed Volume | [Ag] ppb | [Ag] ppb | [Ag] ppb | [Ag] ppb | [Ag] ppb | [Al] ppm |
| 10 | 50 | 28 | 21 | 36 | 52 | |
| 20 | 34 | 10 | 10 | 25 | 37 | 8.956 |
| 30 | 32 | 9 | 5 | 20 | 30 | |
| 40 | 29 | 12 | 4 | 7 | 16 | |
| 50 | 29 | 16 | 5 | 7 | 15 | 0.255 |
| 75 | 38 | 21 | 13 | 20 | 43 | |
| 100 | 35 | 21 | 16 | 29 | 39 | 0.324 |
| 125 | 38 | 23 | 22 | 17 | 31 | |
| 150 | 36 | 23 | 22 | 18 | 33 | 0.235 |
| 175 | 39 | 28 | 26 | 23 | 40 | |
| 200 | 43 | 24 | 25 | 25 | 34 | 0.312 |
| 225 | 40 | 28 | 24 | 28 | 30 | |
| 250 | 44 | 29 | 25 | 29 | 31 | 0.318 |
| 275 | 41 | 31 | 30 | 25 | 32 | |
| 300 | 36 | 32 | 31 | 28 | 33 | 0.321 |
| 325 | 42 | 32 | 35 | 32 | 37 | |
| 350 | 39 | 33 | 37 | 34 | 36 | 0.326 |
| 375 | 40 | 39 | 34 | 36 | 37 | |
| 400 | 45 | 39 | 34 | 33 | 37 | 0.391 |

EXAMPLE 2

Copper Impregnation: Aluminum oxide (Alcan AA300 green bodies sized to 212–300 $\mu$m, 30 mL) was treated with 12 mL of aqueous $Cu(NO_3)_2 \cdot 2\ 1/2H_2O$, which contains an amount of $Cu(NO_3)_2 \cdot 2\ 1/2\ H_2O$ equivalent to 3.66% of the weight of the aluminum oxide. The aluminum oxide and aqueous $Cu(NO_3)_2$ were mixed with a spatula in a 50 mL beaker until all of the aluminum oxide was covered with the liquid. The copper/aluminum oxide composition was allowed to dry at room temperature over night. The composition was then calcined at 100, 250, 350, 450, or 550° C. for one hour as indicated in Table 2.

Reduction of copper/aluminum oxide composition: The copper/aluminum oxide compositions produced above were each treated with ascorbic acid (1.5 g of ascorbic acid for each 25 g of composition in 100 mL of water). Each composition was added to the solution of ascorbic acid while stirring followed by stirring for 5 minutes, and then allowed to stand at room temperature for one hour. The liquid was decanted, and the reduced compositions were washed twice with 100 mL portions of deionized $H_2O$.

Leachability Study: Each of the wet reduced compositions (20 mL) were separately transferred to a column fitted with a stopcock. A solution of $Ca^{2+}$ was prepared by dissolving 0.555 g of $CaCl_2$ in 10 L of $H_2O$ to make a solution 20 ppm in $Ca^{2+}$. The $Ca^{2+}$ solution was allowed to flow through each reduced composition at approximately 10 mL/min (1/2 bed volume/min). A 10 mL sample was collected at pre-selected eluted bed volumes as indicated in Table 2. One drop of concentrated $HNO_3$ was added to each sample as a preservative. These samples were then analyzed by ICP/MS. Table 2 gives the concentration of copper in the effluent in ppb as a function of calcining temperate and bed volume eluted.

TABLE 2

Calcining Time and Temperature for Biocidal Composition Preparation and Leaching Study for Copper and Aluminum.

| Calcining Temp. 1 Hr. Bed Volume | 100° C. [Cu] ppm | 250° C. [Cu] ppm | 350° C. [Cu] ppm | 450° C. [Cu] ppm | 550° C. [Cu] ppm | [Al] ppm |
|---|---|---|---|---|---|---|
| 10 | 42 | 41 | 39 | 0.2 | 0.09 | |
| 20 | 37 | 34 | 64 | 0.067 | 0.15 | 0.32 |
| 30 | 30 | 26 | 60 | 0.039 | 0.17 | |
| 40 | 27 | 22 | 45 | 0.057 | 0.26 | |
| 50 | 25 | 19 | 37 | 0.023 | 0.32 | 0.209 |
| 75 | 6 | 4 | 24 | 0.093 | 0.37 | |
| 100 | 7 | 4 | 2 | 0.18 | 0.23 | 0.21 |
| 125 | 7 | 4 | 2 | 0.17 | 0.19 | |
| 150 | 6 | 4 | 3 | 0.20 | 0.18 | 0.017 |
| 175 | 5 | 3 | 2 | 0.14 | 0.16 | |
| 200 | 4 | 2 | 2 | 0.13 | 0.14 | 0.095 |
| 225 | 3 | 2 | 3 | 0.07 | 0.10 | |
| 250 | 2 | 1 | 2 | 0.086 | 0.089 | 0.118 |
| 275 | 1 | 0.9 | 1 | 0.073 | 0.11 | |
| 300 | 0.45 | 0.62 | 1 | 0.057 | 0.09 | 0.471 |
| 325 | 0.32 | 0.47 | 0.82 | 0.059 | 0.12 | |
| 350 | 0.31 | 0.43 | 0.62 | 0.064 | 0.11 | 0.092 |
| 375 | 0.25 | 0.38 | 0.45 | 0.067 | 0.11 | |
| 400 | 0.21 | 0.32 | 0.29 | 0.071 | 0.11 | 0.186 |

EXAMPLE 3

Comparative Study

Calcine then Copper Impregnation: Aluminum oxide (Alcan AA300 green bodies of sized to 212–300 μm, 48.02 g, 50 mL) was calcined at 550° C. for one hour. The calcined aluminum oxide was allowed to cool to room temperature. The calcined aluminum oxide (25.47 g, 30 mL) was weighed into a 50 mL beaker and treated with a solution of 0.93 g (3.66% of the weight of aluminum oxide) of $Cu(NO_3)_2 \cdot 2\frac{1}{2}H_2OH_2O$ dissolved in 12 mL of deionized $H_2O$. The mixture was stirred with a spatula until all of the aluminum oxide was covered with the blue copper solution. The sample was transferred to a 250 mL beaker and placed into a drying oven for 2 hours at 100° C.

Reduction of copper/aluminum oxide composition: The copper/aluminum oxide composition produced above (21.411 g) was treated with the reducing agent $Na_2S_2O_4$ (0.651 g) of in 100 mL of deionized $H_2O$. The composition was added to the reducing agent with stirring. Upon addition of the composition to the solution, the composition immediately turned dark burgundy in color. The mixture was allowed to stir for approximately 5 minutes. The composition was allowed to sit in the reduction solution for approximately 1 hour after stirring. The liquid was decanted, and the composition was washed twice with 100 mL of de-ionized $H_2O$. The reduced composition was then placed into a drying oven in air for approximately 1 hour at 100° C., during which time, the reduced composition returned to its original green color to produce the oxidized copper/aluminum oxide composition.

Leachability Study : The oxidized copper/aluminum oxide composition was transferred to a column fitted with a stopcock. A solution of $Ca^{2+}$ was prepared by dissolving 0.555 g of $CaCl_2$ in 10 L of $H_2O$ to make a solution 20 ppm in $Ca^{2+}$. The $Ca^{2+}$ solution was allowed to flow through the composition at approximately 10 mL/min ( 1/2 bed volume/min). Approximately 10 mL samples were collected at various bed volumes as indicated in Table 3, one drop of nitric acid was added as a preservative, and the sample was analyzed for copper by ICP/MS.

TABLE 3

Copper Concentration (ppm) in the Effluent as a function of Bed Volume

| Bed Volume | [Cu] (ppm) | [Al] (ppm) |
| --- | --- | --- |
| 10 | 12 | |
| 20 | 10 | 0.10 |
| 30 | 10 | |
| 40 | 8 | |
| 50 | 8 | 0.19 |
| 75 | 6 | |
| 100 | 5 | 0.03 |
| 125 | 4 | |
| 150 | 5 | 0.03 |
| 175 | 3 | |
| 200 | 2 | 0.01 |
| 225 | 2 | |
| 250 | 2 | 0.009 |
| 275 | 2 | |
| 300 | 2 | 0.01 |
| 325 | 2 | |
| 350 | 2 | 0.04 |
| 375 | 1 | |
| 400 | 1 | 0.02 |

EXAMPLE 4

Copper Impregnation: Aluminum oxide (Alcan AA300 green bodies sized to 212–300 μm, was treated with 12 mL of aqueous $Cu(NO_3)_2 \cdot 2 \, 1/2 \, H_2O$ which contains an amount of $Cu(NO_3)_2 \cdot 2 \, 1/2 \, H_2O$ equivalent to 3.66% of the weight of the aluminum oxide and aqueous $Cu(N0_3)_2$ were mixed with a spatula in a 50 mL beaker until all of the aluminum oxide was covered with the liquid. The composition was allowed to dry at room temperature over night. The composition was then calcined 550° C. for one hour.

Reduction of copper/aluminum oxide composition: The copper/aluminum oxide composition produced above (15.588 g) was treated with the reducing agent $Na_2S_2O_4$ (0.486 g) of in 63 mL deionized $H_2O$. The composition was added to the solution with stirring. Upon addition of the composition to the solution, the composition immediatelt turned dark burgundy in color. The mixture was allowed to stir for approximately 5 minutes. The composition was allowed to sit in the reduction solution for approximately 1 hour after stirring. The liquid was decanted, and the reduced composition was washed twice with 100 mL of de-ionized $H_2O$. The reduced composition was then placed into a drying oven in air for approximately 1 hour at 100° C., during which time, the reduced composition to returned to its original green color to produce the oxidized copper/aluminum oxide composition.

Leachability Stud : The oxidized copper/aluminum oxide composition was transferred to a column fitted with a stopcock. A solution of $Ca^{2+}$ was prepared by dissolving 0.555 g of $CaCl_2$ in 10 L of $H_2O$ to make a solution 20 ppm in $Ca^{2+}$. The $Ca^{2+}$ solution was allowed to flow through the composition at approximately 10 mL/min ( 1/2 bed volume/min). Approximately 10 mL samples were collected at various bed volumes as indicated in Table 4, one drop of nitric acid was added as a preservative, and the sample was analyzed for copper by ICP/MS.

TABLE 4

Copper Concentration (ppm) in the Effluent as a function of Bed Volume

| Bed Volume | [Cu] (ppm) | [Al] ppm) |
| --- | --- | --- |
| 10 | 0.11 | |
| 20 | 0.12 | 0.02 |
| 30 | 0.17 | |
| 40 | 0.18 | |
| 50 | 0.20 | 0.02 |
| 75 | 0.24 | |
| 100 | 0.26 | 0.02 |
| 125 | 0.25 | |
| 150 | 0.08 | 0.03 |
| 175 | 0.09 | |
| 200 | 0.08 | 0.01 |
| 225 | 0.11 | |
| 250 | 0.12 | 0.02 |
| 275 | 0.13 | |
| 300 | 0.13 | 0.03 |
| 325 | 0.14 | |
| 350 | 0.13 | 0.02 |
| 375 | 0.16 | |
| 400 | 0.15 | 0.03 |

EXAMPLE 5

Zone of Inhibition Using Biocidal Compositions

The ability of the biocidal compositions of this invention to prevent the growth of bacteria was examined by carrying out zone of inhibition studies as described below. The biocidal compositions used in this example were prepared with the materials indicated in Tables 5 and 6 in a manner similar to that described in examples 1 and 4. All of the support materials are aluminum oxide with the exception of one composition, which has silica gel as the support.

A circle was bored into a 25.0 mL Tryptic Soy Agar or MacConkey Agar plate using a ½ inch diameter cork borer.

The agar was approximately ¼ inch thick in a standard 100 mm×15 mm petri dish. A lawn of E.coli was prepared by dipping the tip of a sterile swab into a broth with $1\times10^4$ CFU/mL or greater of E.coli. The saturated tip was swabbed across the entire surface of the plate. This was achieved by starting at the outer edge of the plate and swabbing evenly towards the center of the plate. Once the center was reached the plate was rotated approximately ⅓ of a full rotation and the swabbing step was repeated. This process was repeated until the entire plate was covered. A spatula was used to remove the bored plug and the hole was packed with the composition to be tested. Using a dropper or 1 mL pipette, two drops of sterile water were added to the composition to aid diffusion. The plates were incubated for 24 hr at 37° C. After incubation the plates were examined for culture growth and any inhibited growth around the perimeter of the composition. If a zone of inhibited growth was found around the composition, it was measured from the outer edge of the biocidal composition to the outer edge of the zone of inhibition. The results are shown in Tables 5 and 6.

TABLE 5

Zone on inhibition produced by copper and silver compositions calcined 550° C. for 2 hours then (1) reduced or (2) reduced and subsequently oxidized in air.

| Support | Biocidal Compound | Particle Size of Support | Reducing Agent | Zone of Inhibition (mm) |
|---|---|---|---|---|
| Alcan AA 300 Green bodies | 5% $Cu(NO_3)_2$ | 212–300 μm | $Na_2S_2O_4$ | 6 |
| Compalox AN/V 801 | 5% $Cu(NO_3)_2$ | 212–300 μm | $Na_2S_2O_4$ | 5 |
| Condea Alumina Beads | 5% $Cu(NO_3)_2$ | 212–300 μm | $Na_2S_2O_4$ | 2 |
| Silica Gel | 5% $Cu(NO_3)_2$ | 200–300 μm | $Na_2S_2O_4$ | 6 |
| Alcoa DD2 | 5% $Cu(NO_3)_2$ | 212–300 μm | $Na_2S_2O_4$ | 5 |
| Alcan AA 300 Green bodies | 5% $Cu(NO_3)_2$ | 212–300 μm | $Na_2S_2O_4$ Then oxidized in air for 2 hr at 100° C. | 6 |
| Compalox AN/V 801 | 5% $Cu(NO_3)_2$ | 212–300 μm | $Na_2S_2O_4$ Then oxidized in air for 2 hr at 100° C. | 4 |
| Condea Alumina Beads | 5% $Cu(NO_3)_2$ | 212–300 μm | $Na_2S_2O_4$ Then oxidized in air for 2 hr at 100° C. | 2 |
| Silica Gel | 5% $Cu(NO_3)_2$ | 200–300 μm | $Na_2S_2O_4$ Then oxidized in air for 2 hr at 100° C. | 5 |
| Alcoa DD2 | 5% $Cu(NO_3)_2$ | 212–300 μm | $Na_2S_2O_4$ Then oxidized in air for 2 hr at 100° C. | 5 |
| Alcan AA 300 Green bodies | 1% $AgNO_3$ | 212–300 μm | Ascorbic acid | 7 |
| Compalox AN/V 801 | 1% $AgNO_3$ | 212–300 μm | Ascorbic acid | 4 |
| Condea Alumina Beads | 1% $AgNO_3$ | 212–300 μm | Ascorbic acid | 5 |
| Silica Gel | 1% $AgNO_3$ | 200–300 μm | Ascorbic acid | 1 |
| Alcoa DD2 | 1% $AgNO_3$ | 212–300 μm | Ascorbic acid | 5 |

TABLE 6

Zone on inhibition produced by copper and silver compositions calcined at 1000° C. for 2 hours then (1) reduced or (2) reduced and subsequently oxidized in air.

| Support | Biocidal Compound | Particle Size of Support | Reducing Agent | Zone of Inhibition (mm) |
|---|---|---|---|---|
| Silica Gel | 1% $AgNO_3$ | 200–300 μm | Ascorbic Acid | N.D. |
| Alcoa DD2 | 1% $AgNO_3$ | 212–300 μm | Ascorbic Acid | N.D. |
| Condea Alumina Beads | 1% $AgNO_3$ | 212–300 μm | Ascorbic Acid | 0.5 |
| Alcan AA 300 Green Bodies | 1% $AgNO_3$ | 212–300 μm | Ascorbic Acid | N.D. |
| Compalox AN/V 801 | 1% $AgNO_3$ | 212–300 μm | Ascorbic Acid | N.D. |
| Alcoa DD2 | 5% $Cu(NO_3)_2$ | 212–30&μm | $Na_2S_2O_4$ | N.D. |
| Silica Gel | 5% $Cu(NO_3)_2$ | 200–300 μm | $Na_2S_2O_4$ | N.D. |
| Condea Alumina Beads | 5% $Cu(NO_3)_2$ | 212–300 μm | $Na_2S_2O_4$ | 1 |
| Compalox AN/V 801 | 5% $Cu(NO_3)_2$ | 212–300 μm | $Na_2S_2O_4$ | N.D. |
| Alcan AA 300 Green Bodies | 5% $Cu(NO_3)_2$ | 212–300 μm | $Na_2S_2O_4$ | N.D. |

N.D. = none detected

EXAMPLE 6

E. Coli were grown overnight in YTN media supplemented with glucose. This culture was used to inoculate 500 mL of YTN, and this second culture was allowed to grow for several hours. The optical density of the culture was followed at 625 nm to estimate the CFU/mL. When the culture was sufficiently dense to provide the proper number of bacteria, the culture was spun down and the bacteria were then resuspended in a solution containing 20 ppm calcium at approximately pH 7.

A small amount of glass wool was gently rolled into a ball and lightly pack into bottom of monster pipette (Fischer Scientific #13-678-8). The pipette was filled with sterile water to ensure that an adequate flow rate of approximately one-drop per second was achieved. The column was packed with 5 grams of the biocidal composition by rinsing the wet composition into the column. Next, the column was pre-washed with 20 mL of water containing 20 ppm calcium at approximately pH 7. A short piece of wide tubing was connected to the top of the column and the other end to a peristaltic pump. The E.Coli suspension to be tested was run through the column at a flow rate of approximately 1/2 bed volume/min and the effluent collected for analysis at desired times. Bacteria were pumped onto the column at concentrations between $1\times10^2$ and $7.0\times10^7$ CFU/mL. A portion of each sample collected (1 mL) was plated onto a MacConkey agar plate and incubated at 37° C. overnight. The plates were read by counting the colonies manually. The remaining sample was in some cases preserved with 1 drop of nitric acid and then analyzed by ICP/MS.

The biocidal composition used in this example was prepared by impregnating compalox aluminum oxide, sized to 212–300 μm, with 3.66% $Cu(NO_3)_2$, calcining at 550° C. for 1 hour, reducing with $Na_2S_2O_4$, then oxidizing in air at 100° C. for 1 hour in a manner similar to that described in Example 4. The results of this experiment are shown in Table 7.

TABLE 7

Compalox alumina impregnated with 3.66% Cu(NO$_3$)$_2$, calcined, 550° C. for 1 hour, reduced with Na$_2$S$_2$O$_4$, then heated to 100° C. in air for 1 hour.

| Bed Volume | Cells CFU/mL Influent | Cells CFU/mL Effluent | % removed | [Cu] (ppb) | [Al] (ppb) |
|---|---|---|---|---|---|
| 20 | 30,000 | 1,425 | 95.2 | 0 | 115 |
| 40 | 30,000 | 1,832 | 93.9 | 40 | 24 |
| 60 | 30,000 | 2,200 | 92.7 | 37 | 27 |
| 80 | 30,000 | 2,400 | 92.0 | 29 | 30 |
| 100 | 30,000 | 5,700 | 81.0 | 5 | 36 |

EXAMPLE 7

The biocidal composition used in this example was prepared by impregnating compalox aluminum oxide, sized to 212–300 μm, with 3.66% Cu(NO$_3$)$_2$, reducing the composition with Na$_2$S$_2$O$_4$, then oxidizing the reduced composition in air at 100° C. for 1 hour in a manner similar to that described in Example 4. A small column was prepared and used as in Example 6. The results of this experiment are shown in Table 8.

TABLE 8

Compalox alumina impregnated with 3.66 % Cu(NO$_3$)$_2$, uncalcined, reduced with Na$_2$S$_2$O$_4$, then heated at 100° C. in air for 1 hour.

| Bed Volume | Cells CFU/mL Influent | Cells CFU/mL Effluent | % removed | [Cu] (ppb) | [Al] (ppb) |
|---|---|---|---|---|---|
| 20 | 140,000 | 3,306 | 97.6 | 761 | 117 |
| 40 | 140,000 | 3,450 | 97.5 | 713 | 0.5 |
| 60 | 140,000 | 3,700 | 97.4 | 1,193 | 387 |
| 80 | 140,000 | 3,540 | 97.5 | 799 | 9 |
| 100 | 140,000 | 3,500 | 97.5 | 745 | 0.3 |

EXAMPLE 8

The biocidal composition used in this example was prepared by impregnating compalox aluminum oxide, sized to 212–300 μm, with 1% AgNO$_3$, calcining at 550° C. for 1 hour, then reducing the composition with ascorbic acid in a manner similar to that described in Example 1. A small column was prepared and used as in example 6. The results of this experiment are shown in Table 9.

TABLE 9

Compalox alumina impregnated with 1% AgNO$_3$, calcined, 550° C. for 1 hour, then reduced with ascorbic acid

| Bed Volume | Cells CFU/mL Influent | Cells CFU/mL Effluent | % removed | [Ag] (ppb) | [Al] (ppb) |
|---|---|---|---|---|---|
| 20 | 30,000 | 14 | 99.9 | 5 | 72 |
| 40 | 30,000 | 62 | 99.8 | 61 | 82 |
| 60 | 30,000 | 75 | 99.8 | 56 | 65 |
| 80 | 30,000 | 164 | 99.4 | 53 | 65 |
| 100 | 30,000 | 210 | 99.3 | 48 | 84 |

EXAMPLE 9

The biocidal composition used in this example was prepared by impregnating compalox aluminum oxide, sized to 212–300 μm, with 1% AgNO3, and the resultant composition was dried overnight at room temperature. The dried composition was then reduced with ascorbic acid in a manner similar to that described in Example 1. A small column was prepared and used as in Example 6. The results of this experiment are shown in Table 10.

TABLE 10

Compalox alumina impregnated with 1% AgNO$_3$, then reduced with ascorbic acid.

| Bed Volume | Cells CFU/mL Influent | Cells CFU/mL Effluent | % removed | [Ag] (ppb) | [Al] (ppb) |
|---|---|---|---|---|---|
| 20 | 140,000 | 78 | 99.9 | 63 | 48 |
| 40 | 140,000 | 120 | 99.9 | 57 | 50 |
| 60 | 140,000 | 250 | 99.8 | 51 | 44 |
| 80 | 140,000 | 295 | 99.8 | 49 | 61 |
| 100 | 140,000 | 310 | 99.8 | 50 | 81 |

EXAMPLE 10

Comparative Study

The biocidal composition used in this example was prepared by impregnating compalox aluminum oxide, sized to 212–300 μm, with 3.66% Cu(NO$_3$)$_2$, and the resultant composition was dried overnight at room temperature in a manner similar to the given in Example 4. The dried composition was not calcined and reduced. A small column was prepared and used as in Example 6. The results of this experiment are shown in Table 11.

TABLE 11

Compalox alumina impregnated with 3.66% Cu(NO$_3$)$_2$

| Bed Volume | Cells CFU/mL Influent | Cells CFU/mL Effluent | % removed | [Cu] (ppb) | [Al] (ppb) |
|---|---|---|---|---|---|
| 20 | 16,000 | 81 | 99.5 | 6,591 | 223.7 |
| 40 | 16,000 | 114 | 99.3 | 5,425 | 135.4 |
| 60 | 16,000 | 125 | 99.2 | 4,313 | 60.5 |
| 80 | 16,000 | 129 | 99.2 | 4,313 | 36.7 |
| 100 | 16,000 | 150 | 99.1 | 3,849 | 17.0 |

EXAMPLE 11

Comparative Study

The biocidal composition used in this example was prepared by impregnating compalox aluminum oxide, sized to 212–300 μm, with 3.66% Cu(NO$_3$)$_2$ and calcining the resultant composition at 550° C. for one hour in a manner similar to the given in Example 4. The composition was not contacted with a reducing agent. A small column was prepared and used as in Example 6. The results of this experiment are shown in Table 12.

TABLE 12

Compalox alumina impregnated with 3.66% Cu(NO$_3$)$_2$ then calcined, 550° C.

| Bed Volume | Cells CFU/mL Influent | Cells CFU/mL Effluent | % removed | [Cu] (ppb) | [Al] (ppb) |
|---|---|---|---|---|---|
| 20 | 9,000 | 22 | 99.8 | 0.81 | 285.7 |
| 40 | 9,000 | 86 | 99.0 | 0.91 | 115.9 |
| 60 | 9,000 | 180 | 98.0 | 1.20 | 102.1 |
| 80 | 9,000 | 200 | 97.8 | 1.43 | 86.8 |
| 100 | 9,000 | 246 | 97.3 | 1.39 | 80.1 |

EXAMPLE 12

Comparative Study

The biocidal composition used in this example was prepared by impregnating compalox aluminum oxide, sized to 212–300 μm, with 1% $AgNO_3$, then calcining the resultant composition at 550° C. for one hour in a manner similar to that in Example 1. The composition was not contacted with a reducing agent. A small column was prepared and used as in Example 6. The results of this experiment are shown in Table 13.

TABLE 13

Compalox alumina impregnated with 1% $AgNO_3$, then calcined at 550° C. for 1 hour.

| Bed Volume | Cells CFU/mL Influent | Cells CFU/mL Effluent | % removed | [Ag] (ppb) | [Al] (ppb) |
|---|---|---|---|---|---|
| 20 | 9,000 | 0 | 100. | 40.4 | 3,220 |
| 40 | 9,000 | 7 | 99.9 | 40.0 | 259.4 |
| 60 | 9,000 | 31 | 99.7 | 50.3 | 160.7 |
| 80 | 9,000 | 22 | 99.7 | 35.0 | 138.1 |
| 100 | 9,000 | 40 | 99.6 | 31.1 | 115.0 |

EXAMPLE 13

Comparative Study

The biocidal composition used in this example was prepared by impregnating compalox aluminum oxide, sized to 212–300 μm, with 1% $AgNO_3$, and the resultant composition was dried overnight at room temperature in a manner similar to the procedure in Example 1. The dried composition was not calcined and reduced. A small column was prepared and used as in Example 6. The results of this experiment are given in Table 14.

TABLE 14

Compalox alumina impregnated with 1% $AgNO_3$.

| Bed Volume | Cells CFU/mL Influent | Cells CFU/mL Effluent | % removed | [Ag] (ppb) | [Al] (ppb) |
|---|---|---|---|---|---|
| 20 | 16,000 | 0 | 100.0 | 40.0 | 413.9 |
| 40 | 16,000 | 0 | 100.0 | 31.4 | 268.4 |
| 60 | 16,000 | 1 | 99.9 | 29.1 | 142.1 |
| 80 | 16,000 | 4 | 999 | 28.1 | 19.1 |
| 100 | 16,000 | 6 | 99.9 | 28.4 | 106.9 |

EXAMPLE 4

In a mini column that was packed and used as described in Example 6, 1 part by weight of reduced copper/aluminum oxide composition (1.7 g compalox alumina, sized to 212–300 μm, that was impregnated with 3.66% $Cu(NO_3)_2$, calcined at 550° C. for 1 hour, then reduced with $Na_2S_2O_4$ using the procedure in Example 4) was placed over 2 parts by weight reduced silver/aluminum oxide composition (3.3 g compalox aluminum oxide, sized to 212–300 μm, that was impregnated with 1% $AgNO_3$, calcined, 550° C. for 1 hour, then reduced with ascorbic acid using the procedure in Example 1 ) to produce a two layer system. The liquid containing the *E. Coli* was first passed through the reduced copper/aluminum oxide composition, then through the reduced silver/aluminum oxide composition. The column was run as in Example 6. The results of this experiment are shown in Table 15.

TABLE 15

1 part compalox alumina impregnated with 3.66% $Cu(NO_3)_2$, calcined at 550° C. for 1 hour, then reduced with $Na_2S_2O_4$: 2 parts compalox alumina impregnated with 1% $AgNO_3$, calcined at 550° C. for 1 hour, then reduced with ascorbic acid.

| Bed Volume | Cells CFU/mL effluent | Cells CFU/mL Influent | % removed | [Ag] (ppb) | [Cu] (ppb) | [Al] (pbb) |
|---|---|---|---|---|---|---|
| 20 | 8 | 120,000 | 99.9 | 28.1 | 0.18 | 125. |
| 40 | 23 | 120,000 | 99.9 | 31.8 | 0.82 | 61.3 |
| 60 | 84 | 120,000 | 99.9 | 28.7 | 0.66 | 49.9 |
| 80 | 156 | 120,000 | 99.9 | 25.5 | 0.11 | 37.3 |
| 100 | 43 | 120,000 | 99.9 | 21.5 | N.D. | 15.4 |
| 160 | 75 | 120,000 | 99.9 | 20.1 | 0.10 | 86.3 |
| 580 | 8 | 120000 | 99.9 | 23.8 | 0.49 | 437 |
| 630 | 168 | 120,000 | 99.9 | 22.8 | 0.14 | 129 |

EXAMPLE 15

Standard bacteria suspensions of *E. Coli* (ATCC-25922) were prepared by growing the bacteria overnight in YTN media supplemented with glucose. The overnight culture is used to inoculate 500 mL of YTN. The large bacterial culture is grown for several hours and the optical density followed at 625 nm. When the culture is of sufficient optical density at 625 nm to provide the proper number of bacteria the culture is spun down and the bacteria resuspended in a solution containing 20 ppm calcium. The bacterial solution is pumped onto the column at concentrations between $1 \times 10^4$ and $7.0 \times 10^7$ colony forming units (CFU) per mil, at a predetermined flow rate (1/3-1 bed volume/min). Samples of the column effluent (50 mL) were collected at predetermined intervals. A 1 mL sample of effluent was plated onto MacConkey agar plates and incubated at 37° C. overnight. The remaining sample was analyzed for metals by ICM/MS.

The biocidal composition used in this example was prepared by impregnating aluminum oxide (Alcan AA300 alumina green bodies alumina, sized to 212–300 μm), with 1% $AgNO_3$, calcining the composition at 550° C. for 2 hours, then reducing the composition with ascorbic acid in a manner similar to that described in Example 1. The column was run with 80 g of reduced composition in a 1 inch diameter column at a flow rate of approximately 1/3 bed volume/min as described above. The results of this experiment are shown in Table 6.

TABLE 16

Aluminum oxide impregnated with 1% $AgNO_3$, calcined at 550° C. for 2 hours, then reduced with ascorbic acid.

| Bed Volume | Cells CFU/mL Influent | Cells CFU/mL Effluent | % removed |
|---|---|---|---|
| 20 | 250,000 | 0 | 100.00 |
| 40 | 250,000 | 0 | 100.00 |
| 60 | 250,000 | 0 | 100.00 |
| 80 | 250,000 | 0 | 100.00 |
| 100 | 250,000 | 1 | 99.9 |
| 130 | 140,000 | 4 | 99.9 |
| 150 | 140,000 | 14 | 99.9 |
| 430 | 140,000 | 144 | 99.9 |
| 480 | 80,000 | 180 | 99.8 |
| 530 | 80,000 | 192 | 99.8 |
| 580 | 80,000 | 734 | 99.1 |
| 630 | 80,000 | 542 | 99.3 |
| 680 | 80,000 | 846 | 98.9 |
| 730 | 80,000 | 1,244 | 98.4 |

EXAMPLE 16

A mini column was packed and run as described in Example6 with1 part by weight of reduced copper/ aluminum oxide composition and 2 parts by weight reduced silver/aluminum oxide composition, wherein the reduced copper/aluminum oxide composition was placed over the reduced silver/aluminum oxide composition. The reduced copper/aluminum oxide composition was produced as follows: (1) aluminum oxide (1.7 g Alcan AA400, sized to 212–300 µm) was impregnated with a sufficient amount of $Cu(NO_3)_2$ to give a 6.5% copper composition upon calcining at 550° C. for 4 hours to produce an impregnated copper/aluminum oxide composition; and (2) the impregnated copper/aluminum oxide composition was contacted with $Na_2S_2O_4$ and then heated using the procedure in Example 4 to produce the reduced copper/aluminum oxide composition. The reduced silver/aluminum oxide composition was prepared as follows: aluminum oxide (3.3 g Condea Pural, sized to 100–300 µm) was impregnated with 1% $AgNO_3$, calcined 550° C. for 1 hour, then reduced with ascorbic acid using the procedure in Example 1 to produce the reduced silver aluminum oxide composition.

The liquid containing the *E. Coli* was first passed through the reduced copper/aluminum oxide composition, then through the reduced silver/aluminum oxide composition at 1/2 bed volumes/min. The column was run as in Example 6, and the results are given in Table 17.

TABLE 17

Two Layer System Composed of 1 part by weight of reduced copper/aluminum oxide composition and 2 parts by weight reduced silver/aluminum oxide composition, wherein the reduced copper/aluminum oxide composition was placed over the reduced silver/aluminum oxide composition.

| Bed Volume | Cells CFU/mL effluent | Cells CFU/mL Influent | % removed | [Ag] (ppb) | [Cu] (ppb) |
|---|---|---|---|---|---|
| 20 | $1.1 \times 10^5$ | 4 | 99.9 | 2.5 | 0.7 |
| 40 | $1.1 \times 10^5$ | 3 | 99.9 | N.D. | N.D. |
| 60 | $1.2 \times 10^5$ | 3 | 99.9 | 0.4 | 4.0 |
| 80 | $1.2 \times 10^5$ | 3 | 99.9 | | N.D. |
| 330 | $1.2 \times 10^5$ | 1 | 99.9 | 4.2 | N.D. |
| 430 | $1.2 \times 10^5$ | 431 | 99.9 | 5.8 | 4.8 |
| 490 | $1.2 \times 10^5$ | 650 | 99.9 | 3.1 | 10.6 |
| 530 | $1.2 \times 10^5$ | 197 | 99.9 | 3.9 | 4.8 |
| 550 | $1.2 \times 10^5$ | 390 | 99.9 | 3.2 | 12.8 |

EXAMPLE 17

A mini column was packed and run as described in Example 6 with 1 part by weight of reduced copper/aluminum oxide composition and 2 parts by weight reduced silver/aluminum oxide composition, wherein the reduced copper/aluminum oxide composition was placed over the reduced silver/aluminum oxide composition. The reduced copper/aluminum oxide composition was produced as follows: (1) aluminum oxide (1.7 g Alcan AA400, sized to 212–300 µm) was impregnated with a sufficient amount of $Cu(NO_3)_2$ to give a 6.5% copper composition upon calcining at 550° C. for 4 hours to produce an impregnated copper/aluminum oxide composition; and (2) the impregnated copper/aluminum oxide composition was contacted with $Na_2S_2O_4$ and then heated using the procedure in Example 4 to produce the reduced copper/aluminum oxide composition. The reduced silver/aluminum oxide composition was prepared as follows: aluminum oxide (3.3 g Condea Pural, sized to 100–300 µm) was impregnated with 1% $AgNO_3$, calcined 550° C. for 1 hour, then reduced with ascorbic acid using the procedure in Example 1 to produce the reduced silver aluminum oxide composition.

The liquid containing the *E. Coli* was first passed through the reduced copper/aluminum oxide composition, then through the reduced silver/aluminum oxide composition at 1/2 bed volumes/min. The column was run as in Example 6, and the results are given in Table 18.

TABLE 18

Two Layer System Composed of 1 part by weight of reduced copper/aluminum oxide composition and 2 parts by weight reduced silver/aluminum oxide composition, wherein the reduced copper/aluminum oxide composition was placed over the reduced silver/aluminum oxide composition.

| Bed Volume | Cells CFU/mL effluent | Cells CFU/mL Influent | % removed | [Ag] (ppb) | [Cu] (ppb) | [Al] (pbb) |
|---|---|---|---|---|---|---|
| 20 | $7 \times 10^2$ | 0 | 100 | 81.9 | 27.3 | 49.6 |
| 40 | $7 \times 10^2$ | 0 | 100 | 85.8 | 10.6 | 24.1 |
| 60 | $7 \times 10^2$ | 0 | 100 | 71.1 | 12.4 | 26.0 |
| 80 | $7 \times 10^2$ | 0 | 100 | 72.5 | 12.5 | 21.0 |
| 100 | $7 \times 10^2$ | 0 | 100 | 67.0 | 10.2 | 21.8 |
| 150 | $7 \times 10^2$ | 0 | 100 | 65.1 | 10.7 | 14.6 |
| 360 | $7 \times 10^2$ | 0 | 100 | 50.8 | 18.0 | 7.7 |
| 480 | $7 \times 10^2$ | 0 | 100 | — | — | — |
| 500 | $7 \times 10^2$ | 0 | 100 | — | — | — |

EXAMPLE 18

A mini column was packed and run as described in Example 6 with 1 part by weight manganese dioxide/aluminum oxide composition and 2 parts by weight reduced silver/aluminum oxide composition, wherein the manganese dioxide/aluminum oxide composition was placed over the reduced silver/aluminum oxide composition. The manganese dioxide/aluminum oxide composition was prepared by the process disclosed in international publication WO 97/47380, wherein 5% by weight $MnO_2$, 25% colloidal aluminum oxide (Condea disperal P2), and 70% Versal GH aluminum oxide (calcined at 550° C. for 1.5 hours) was admixed with acetic acid (60 mL of 7% acetic acid per 100 g of dry material used). The reduced silver/aluminum oxide composition was prepared by impregnating aluminum oxide (3.3 g Condea Pural NW aluminum oxide, sized to 100–300 µm) with 1% $AgNO_3$, calcining the silver/aluminum oxide composition at 550° C. for 1 hour, then reducing the silver/aluminum oxide composition with ascorbic acid using the procedure in Example 1 to produce the reduced silver/aluminum oxide composition.

The liquid containing the *E. Coli* was first passed through manganese dioxide/aluminum oxide composition, then through the reduced silver/aluminum oxide composition at 1/3 bed volumes/min. The column was run as in Example 6 the results are given in Table 19.

TABLE 19

Two Layer System Composed of 1 part by weight manganese dioxide/aluminum oxide composition and 2 parts by weight reduced silver/aluminum oxide composition, wherein the manganese dioxide/aluminum oxide composition was placed over the reduced silver/aluminum oxide composition.

| Bed Volume | Cells CFU/mL effluent | Cells CFU/mL Influent | % removed | [Ag] (ppb) | [Mn] (ppb) | [Al] (pbb) |
|---|---|---|---|---|---|---|
| 20 | $2.7 \times 10^5$ | 0 | 100 | 50.1 | 110. | 10.4 |
| 40 | $2.7 \times 10^5$ | 0 | 100 | 41.4 | 69.3 | 8.4 |
| 60 | $2.7 \times 10^5$ | 1 | 99.9 | 35.3 | 28.8 | 53.7 |

TABLE 19-continued

Two Layer System Composed of 1 part by weight manganese dioxide/aluminum oxide composition and 2 parts by weight reduced silver/aluminum oxide composition, wherein the manganese dioxide/aluminum oxide composition was placed over the reduced silver/aluminum oxide composition.

| Bed Volume | Cells CFU/mL effluent | Cells CFU/mL Influent | % removed | [Ag] (ppb) | [Mn] (ppb) | [Al] (pbb) |
|---|---|---|---|---|---|---|
| 80 | 2.7 × 10$^5$ | 1 | 99.9 | 24.1 | 11.0 | 33.6 |
| 360 | 1.0 × 10$^5$ | 69 | 99.9 | 13.9 | 1.4 | 90.2 |
| 410 | 9.0 × 10$^4$ | 28 | 99.9 | — | — | — |
| 460 | 1.1 × 10$^5$ | 18 | 99.9 | — | — | — |

EXAMPLE 19

Aluminum oxide (Alcan AA400G sized to 212–300 μm, 30 mL) was admixed with aqueous solution of Cu(NO$_3$)$_2$.2 1/2 H$_2$O, then calcined at 550° C. for 1 hour. The resultant composition was then reduced with Na$_2$S$_2$O$_4$, then oxidized in air in a manner similar to that described in Example 4.

Approximately 1.5 g of the oxidized copper/aluminum oxide composition was placed in a Cahn TG-151 TGA. The composition was held in a platinum mesh basket fabricated in-house in order to maximize contact between the adsorbent and the reactive gases. All weight gains and losses are reported in wt % relative to the initial composition weight. The composition was heated in methane at 500° C. for 30 minutes. This step is the preliminary "regeneration" step. The regeneration step provides a consistent initial oxidation state of the active adsorbent for all subsequent measurements, regardless of the initial form of the composition. The composition is then cooled to 150° C. in flowing nitrogen. The composition was then exposed to a SO$_2$ mixture, which contains 3,000 ppmof SO$_2$ and 2% oxygen in nitrogen, for one hour. After this, the composition is exposed to flowing nitrogen for 15 minutes to purge the system. The flow is then switched to pure methane and the sample heated to 500° C. and held at that temperature for 30 minutes to regenerate the composition. Complete regeneration of the surface adsorption capacity of the composition is realized by this method. This cycle is then repeated as needed to investigate loss of capacity as a function of regeneration cycle. The composition adsorbed 2.13 wt % SO$_2$ in the first cycle, 2.67 wt % SO$_2$ in the second cycle, and 2.57 wt % SO$_2$ in the third cycle.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed:

1. A process for producing a composition containing a biocidal compound, comprising:
   (a) admixing a support comprising a metal oxide with a first biocidal compound comprising copper nitrate to produce a mixture;
   (b) heating the mixture produced in step (a) at from 80 to 1,800° C. to produce a heated mixture; and
   (c) contacting the heated mixture produced in step (b) with a reducing agent comprising sodium dithionate to reduce at least some of the first biocidal compound to produce a first reduced biocidal/support composition.

2. The process of claim 1, wherein the metal oxide is an adsorbent and/or catalyst compound.

3. The process of claim 1, wherein the metal oxide comprises a transition metal oxide, a lanthanide oxide, a Group IIA oxide, a Group IIIA oxide, a Group IVA oxide, a Group VA oxide, or a combination thereof.

4. The process of claim 1, wherein the metal oxide comprises an oxide of aluminum, titanium, copper, vanadium, silicon, manganese, iron, zinc, zirconium, magnesium, thorium, or a combination thereof.

5. The process of claim 1, wherein the metal oxide comprises zeolite.

6. The process of claim 1, wherein the metal oxide comprises Al$_2$O$_3$, TiO$_2$, CuO, Cu$_2$O, V$_2$O$_5$, SiO$_2$, MnO$_2$, Mn$_3$O$_4$, ZnO, MgO, ThO$_2$, or a combination thereof.

7. The process of claim 1, wherein the support is aluminum oxide.

8. The process of claim 1, wherein the support is silicon dioxide.

9. The process of claim 1, wherein the support is an oxide of magnesium.

10. The process of claim 1, wherein the admixing step comprises mixing the support with a first biocidal compound/solvent system.

11. The process of claim 1, wherein the first biocidal compound further comprises a silver compound.

12. The process of claim 1, wherein the support is from 0.1 to 99.9% by weight and the first biocidal compound is from 0.1 to 99.9% by weight, wherein the sum of the support and the first biocidal compound is 100%.

13. The process of claim 1, wherein after step (a) and prior to step (b), drying the mixture at from 20 to 50° C.

14. The process of claim 1, wherein the heating step (b) is conducted at from 200 to 1,800° C.

15. The process of claim 1, wherein the support is aluminum oxide calcined at from 200 to 700° C. and the first biocidal compound comprises copper nitrate.

16. The process of claim 1, wherein the support is aluminum oxide, the first biocidal compound is Cu(NO$_3$)$_2$.2.5 H$_2$O, the heating step (b) is from 100 to 700° C., and the reducing agent is sodium dithionate.

17. The process of claim 1, wherein after step (c),
   (d) admixing the first reduced biocidal/support composition with a binder comprising a colloidal metal oxide or colloidal metalloid oxide and an acid, and
   (e) removing a sufficient amount of water from the admixture to cross-link the binder with itself and/or the first reduced biocidal/support composition to produce a binder/biocidal composition.

18. The process of claim 17, wherein after step (e), admixing the binder/biocidal composition with a second biocidal compound.

19. The process of claim 1, wherein after step (c), admixing the first reduced biocidal/support composition with a second biocidal compound to produce a second biocidal/support composition.

20. The process of claim 19, further comprising contacting the second biocidal/support composition with a reducing agent to reduce at least some of the second biocidal compound to produce a second reduced biocidal/support composition.

21. The process of claim 20, further comprising oxidizing at least some of the second biocidal compound in the second reduced biocidal/support composition.

22. The process of claim 21, wherein the oxidizing step comprises contacting the second reduced biocidal/support composition with an oxidizing agent, wherein the oxidizing agent comprises oxygen, ozone, hydrogen peroxide, $ClO_2$, $ClO_3^-$, air, or a combination thereof.

23. The method of claim 21, wherein the oxidizing step comprises heating the second reduced biocidal/support composition in air at from 80 to 1,500° C.

24. A process for producing a composition containing a biocidal compound comprising:
(a) admixing a support comprising a metal oxide with a first biocidal compound comprising copper nitrate to produce a mixture;
(b) heating the mixture produced in step (a) at from 80 to 1,800° C. to produce a heated mixture;
(c) contacting the heated mixture produced in step (b) with a reducing agent comprising sodium dithionate to reduce at least some of the first biocidal compound to produce a first reduced biocidal/support composition; and
(d) oxidizing at least some of the first biocidal compound in the first reduced biocidal/support composition to produce a first oxidized biocidal/support composition.

25. The process of claim 24, wherein the metal oxide is an adsorbent and/or catalyst compound.

26. The method of claim 24, wherein step (d) comprises heating the reduced biocidal/support composition in air at from 80 to 1,500° C.

27. The method of claim 24, wherein the support is aluminum oxide, the biocidal compound is $Cu(NO_3)_2 \cdot 2.5\ H_2O$, the heating step (b) is from 400 to 700° C., the reducing agent is $Na_2S_2O_4$, and the oxidizing step comprises heating the reduced biocidal/support composition in air from 90 to 110° C.

28. The process of claim 24, wherein after step (d),
(e) admixing the first oxidized biocidal/support composition with a binder comprising a colloidal metal oxide or colloidal metalloid oxide and an acid, and
(f) removing a sufficient amount of water from the admixture to cross-link the binder with itself and/or the first oxidized biocidal/support composition to produce a binder/biocidal composition.

29. The process of claim 28, wherein after step (f), admixing the binder/biocidal composition with a second biocidal compound.

30. The process of claim 24, wherein after step (d), admixing the first oxidized biocidal/support composition with a second biocidal compound to produce a second biocidal/support composition.

31. The process of claim 30, further comprising contacting the second biocidal/support composition with a reducing agent to reduce at least some of the second biocidal compound to produce a reduced biocidal/support composition.

32. The process of claim 31, further comprising oxidizing at least some of the second biocidal compound in the reduced biocidal/support composition.

33. The process of claim 24, wherein prior to step (a), the metal oxide is (1) calcined at a particle temperature of from 200 to 700° C., and (2) contacted with a dilute acid, wherein the acid contacting is more than a surface wash but less than an etching, wherein the resultant acid treated metal oxide is not subsequently calcined.

34. The process of claim 24, wherein the support is aluminum oxide.

35. The process of claim 24, wherein the support is silicon dioxide.

36. The process of claim 24, wherein the support is an oxide of magnesium.

37. A process for producing a composition containing a biocidal compound, comprising:
(a) admixing a support comprising a metal oxide with a biocidal compound comprising copper nitrate to produce a mixture;
(b) drying the mixture to produce a dried mixture; and
(c) contacting the dried mixture produced in step (b) with a reducing agent comprising sodium dithionate to reduce at least some of the biocidal compound to produce a reduced biocidal/support composition.

38. The process of claim 37 wherein the metal oxide is an adsorbent and/or catalyst compound.

39. The process of claim 37, wherein the drying step is conducted at from 20 to 30° C.

40. A process for producing a composition containing a biocidal compound comprising:
(a) admixing components comprising:
(1) a support comprising a metal oxide;
(2) a binder comprising a colloidal metal oxide or colloidal metalloid oxide;
(3) a first biocidal compound comprising copper nitrate; and
(4) an acid;
(b) removing a sufficient amount of water to cross-link the binder with itself, the support, and/or the first biocidal compound to produce a first binder/biocidal composition; and
(c) contacting the first binder/biocidal composition produced in step (b) with a reducing agent comprising sodium dithionate to reduce at least some of the first biocidal compound to produce a first reduced biocidal/support composition.

41. The process of claim 40, wherein the metal oxide of the support is an adsorbent and/or catalyst compound.

42. The process of claim 40, further comprising oxidizing at least some of the first biocidal compound in the first reduced binder/biocidal composition to produce a first oxidized binder/biocidal composition.

43. The process of claim 40, wherein after step (c), admixing the first reduced binder/biocidal composition with a second biocidal compound to produce a second binder/biocidal composition.

44. The process of claim 43, further comprising contacting the second binder/biocidal composition with a reducing agent to reduce at least some of the second biocidal compound to produce a second reduced binder/biocidal composition.

45. The process of claim 44, further comprising oxidizing at least some of the second biocidal compound in the second reduced binder/biocidal composition.

46. The process of claim 41, wherein prior to step (a), the metal oxide of the support is (1) calcined at a particle temperature of from 200 to 700° C., and (2) contacted with a dilute acid, wherein the acid contacting is more than a surface wash but less than an etching, wherein the resultant acid treated metal oxide is not subsequently calcined.

47. The process of claim 46, wherein the metal oxide of the support is aluminum oxide.

48. The process of claim 40, wherein the support is aluminum oxide.

49. The process of claim 40, wherein the support is silicon dioxide.

50. The process of claim 40, wherein the support is an oxide of magnesium.

51. The process of claim 40, wherein after step (c), the first reduced biocidal/support composition is heated in air at from 80 to 1,500° C.

52. A process for producing a composition containing a biocidal compound comprising:
(a) admixing components comprising:
(i) a binder comprising a colloidal metal oxide or colloidal metalloid oxide,
(ii) a support comprising a metal oxide, and
(iii) an acid,
to produce a mixture,
(b) removing a sufficient amount of water from the mixture produced in step (a) to cross-link the binder with itself and/or the support to produce a binder/support system; and
(c) admixing the binder/support system produced in step (b) with a first biocidal compound comprising copper nitrate to produce a first binder/biocidal composition.

53. The process of claim 52, wherein the metal oxide of the support is an adsorbent and/or catalyst compound.

54. The process of claim 52, wherein after step (c), contacting the first binder/biocidal composition with a reducing agent comprising sodium dithionate to reduce at least some of the first biocidal compound to produce a reduced binder/biocidal composition.

55. The process of claim 54, further comprising oxidizing at least some of the first biocidal compound in the reduced binder/biocidal composition.

56. The process of claim 52, wherein prior to step (a), the metal oxide of the support is ( 1) calcined at a particle temperature of from 200 to 700° C., and ( 2) contacted with a dilute acid, wherein the acid contacting is more than a surface wash but less than an etching, wherein the resultant acid treated metal oxide is not subsequently calcined.

57. The process of claim 56, wherein the metal oxide of the support is aluminum oxide.

58. The process of claim 52, wherein the support is aluminum oxide.

59. The process of claim 52, wherein the support is an silicon dioxide.

60. A process of claim 52, wherein the support is an oxide magnesium.

61. A process for producing a composition containing an adsorbent and/or catalyst compound, comprising:
(a) admixing a support comprising a metal oxide with a first adsorbent and/or catalyst compound comprising copper nitrate to produce a mixture;
(b) heating the mixture produced in step (a) at from 80 to 1,800° C. to produce a heated mixture; and
(c) contacting the heated mixture produced in step (b) with a reducing agent comprising sodium dithionate to reduce at least some of the first adsorbent and/or catalyst compound to produce a first reduced adsorbent and/or catalyst/support composition.

62. A process for producing a composition containing an adsorbent and/or catalyst compound, comprising:
(a) admixing a support comprising a metal oxide with a first adsorbent and/or catalyst compound comprising copper nitrate to produce a mixture;
(b) heating the mixture produced in step (a) at from 80 to 1,800° C. to produce a heated mixture;
(c) contacting the heated mixture produced in step (b) with a reducing agent comprising sodium dithionate to reduce at least some of the first adsorbent and/or catalyst compound to produce a reduced adsorbent and/or catalyst/support composition; and
(d) oxidizing at least some of the first adsorbent and/or catalyst compound in the reduced adsorbent and/or catalyst/support composition to produce an oxidized adsorbent and/or catalyst/support composition.

63. A process for producing a composition containing an adsorbent and/or catalyst compound, comprising:
(a) admixing a support comprising a metal oxide with an adsorbent and/or catalyst compound comprising copper nitrate to produce a mixture;
(b) drying the mixture to produce a dried mixture; and
(c) contacting the dried mixture produced in step (b) with a reducing agent comprising sodium dithionate to reduce at least some of the adsorbent and/or catalyst compound to produce a reduced adsorbent and/or catalyst compound/support composition.

64. A process for producing a composition containing an adsorbent and/or catalyst compound comprising:
(a) admixing components comprising:
(1) a support comprising a metal oxide;
(2) a binder comprising a colloidal metal oxide or colloidal metalloid oxide;
(3) a first adsorbent and/or catalyst compound comprising copper nitrate; and
(4) an acid;
(b) removing a sufficient amount of water to cross-link the binder with itself, the support, and/or the adsorbent and/or catalyst compound to produce a first binder/adsorbent and/or catalyst composition; and
(c) contacting the first binder/adsorbent and/or catalyst composition produced in step (b) with a reducing agent comprising sodium dithionate to reduce at least some of the first adsorbent and/or catalyst compound to produce a first reduced adsorbent and/or catalyst/support composition.

65. A process for producing a composition containing an adsorbent and/or catalyst compound comprising:
(a) admixing components comprising:
(i) a binder comprising a colloidal metal oxide or colloidal metalloid oxide,
(ii) a support comprising a metal oxide, and
(iii) an acid,
to produce a mixture,
(b) removing a sufficient amount of water from the mixture produced in step (a) to cross-link the binder with itself and/or the support to produce a binder/support system; and
(c) admixing the binder/support system produced in step (b) with a first adsorbent and/or catalyst compound comprising copper nitrate to produce a first binder/adsorbent and/or catalyst composition.

66. A process for producing a composition containing a biocidal compound, comprising:
(a) admixing a support comprising a metal oxide with a first biocidal compound comprising silver nitrate to produce a mixture;
(b) heating the mixture produced in step (a) at from 80 to 1,800° C. to produce a heated mixture; and
(c) contacting the heated mixture produced in step (b) with a reducing agent comprising ascorbic acid to reduce at least some of the first biocidal compound to produce a first reduced biocidal/support composition.

67. The process of claim 66, wherein the metal oxide is an adsorbent and/or catalyst compound.

68. The process of claim 66, wherein the metal oxide comprises a transition metal oxide, a lanthanide oxide, a Group IIA oxide, a Group IIIA oxide, a Group IVA oxide, a Group VA oxide, or a combination thereof.

69. The process of claim 66, wherein the metal oxide comprises an oxide of aluminum, titanium, copper, vanadium, silicon, manganese, iron, zinc, zirconium, magnesium, thorium, or a combination thereof.

70. The process of claim 66, wherein the metal oxide comprises zeolite.

71. The process of claim 66, wherein the metal oxide comprises $Al_2O_3$, $TiO_2$, CuO, $Cu_2O$, $V_2O_5$, $SiO_2$, $MnO_2$, $Mn_3O_4$, ZnO, MgO, $ThO_2$, or a combination thereof.

72. The process of claim 66, wherein the support is aluminum oxide.

73. The process of claim 66, wherein the support is silicon dioxide.

74. The process of claim 66, wherein the support is an oxide of magnesium.

75. The process of claim 66, wherein the admixing step comprises mixing the support with a first biocidal compound/solvent system.

76. The process of claim 66, wherein the first biocidal compound further comprises a copper compound.

77. The process of claim 66, wherein the support is from 0.1 to 99.9% by weight and the first biocidal compound is from 0.1 to 99.9% by weight, wherein the sum of the support and the first biocidal compound is 100%.

78. The process of claim 66, wherein after step (a) and prior to step (b), drying the mixture at from 20 to 50° C.

79. The process of claim 66, wherein the heating step (b) is conducted at from 200 to 1,800° C.

80. The process of claim 66, wherein the support is aluminum oxide calcined at from 200 to 700° C. and the first biocidal compound comprises silver nitrate.

81. The process of claim 66, wherein the support is aluminum oxide, the first biocidal compound is $AgNO_3$, the heating step (b) is from 100 to 700° C., and the reducing agent is ascorbic acid.

82. The process of claim 66, wherein after step (c),
(d) admixing the first reduced biocidal/support composition with a binder comprising a colloidal metal oxide or colloidal metalloid oxide and an acid, and
(e) removing a sufficient amount of water from the admixture to cross-link the binder with itself and/or the first reduced biocidal/support composition to produce a binder/biocidal composition.

83. The process of claim 82, wherein after step (e), admixing the binder/biocidal composition with a second biocidal compound.

84. The process of claim 66, wherein after step (c), admixing the first reduced biocidal/support composition with a second biocidal compound to produce a second biocidal/support composition.

85. The process of claim 84, further comprising contacting the second biocidal/support composition with a reducing agent to reduce at least some of the second biocidal compound to produce a second reduced biocidal/support composition.

86. The process of claim 85, further comprising oxidizing at least some of the second biocidal compound in the second reduced biocidal/support composition.

87. The process of claim 86, wherein the oxidizing step comprises contacting the second reduced biocidal/support composition with an oxidizing agent, wherein the oxidizing agent comprises oxygen, ozone, hydrogen peroxide, $ClO_2$, $ClO_3^-$, air, or a combination thereof.

88. The process of claim 86, wherein the oxidizing step comprises heating the second reduced biocidal/support composition in air at from 80 to 1,500° C.

89. A process for producing a composition containing a biocidal compound comprising:
(a) admixing a support comprising a metal oxide with a first biocidal compound comprising silver nitrate to produce a mixture;
(b) heating the mixture produced in step (a) at from 80 to 1,800° C. to produce a heated mixture;
(c) contacting the heated mixture produced in step (b) with a reducing agent comprising ascorbic acid to reduce at least some of the first biocidal compound to produce a first reduced biocidal/support composition; and
(d) oxidizing at least some of the first biocidal compound in the first reduced biocidal/support composition to produce a first oxidized biocidal/support composition.

90. The process of claim 89, wherein the metal oxide is an adsorbent and/or catalyst compound.

91. The method of claim 89, wherein step (d) comprises heating the reduced biocidal/support composition in air at from 80 to 1,500° C.

92. The process of claim 89, wherein after step (d),
(e) admixing the first oxidized biocidal/support composition with a binder comprising a colloidal metal oxide or colloidal metalloid oxide and an acid, and
(f) removing a sufficient amount of water from the admixture to cross-link the binder with itself and/or the first oxidized biocidal/support composition to produce a binder/biocidal composition.

93. The process of claim 92, wherein after step (f), admixing the binder/biocidal composition with a second biocidal compound.

94. The process of claim 89, wherein after step (d), admixing the first oxidized biocidal/support composition with a second biocidal compound to produce a second biocidal/support composition.

95. The process of claim 94, further comprising contacting the second biocidal/support composition with a reducing agent to reduce at least some of the second biocidal compound to produce a reduced biocidal/support composition.

96. The process of claim 95, further comprising oxidizing at least some of the second biocidal compound in the reduced biocidal/support composition.

97. The process of claim 89, wherein prior to step (a), the metal oxide is (1) calcined at a particle temperature of from 200 to 700° C., and (2) contacted with a dilute acid, wherein the acid contacting is more than a surface wash but less than an etching, wherein the resultant acid treated metal oxide is not subsequently calcined.

98. The process of claim 89, wherein the support is aluminum oxide.

99. The process of claim 89, wherein the support is silicon dioxide.

100. The process of claim 89, wherein the support is an oxide of magnesium.

101. A process for producing a composition containing a biocidal compound, comprising:
(a) admixing a support comprising a metal oxide with a biocidal compound comprising silver nitrate to produce a mixture;
(b) drying the mixture to produce a dried mixture; and
(c) contacting the dried mixture produced in step (b) with a reducing agent comprising ascorbic acid to reduce at least some of the biocidal compound to produce a reduced biocidal/support composition.

102. The process of claim 101, wherein the metal oxide is an adsorbent and/or catalyst compound.

103. The process of claim 101, wherein the drying step is conducted at from 20 to 30° C.

104. The process of claim 101, wherein the support is aluminum oxide, the biocidal compound is AgNO$_3$, the drying step is from 20 to 50° C., and the reducing agent is ascorbic acid.

105. A process for producing a composition containing a biocidal compound comprising:
(a) admixing components comprising:
  (1) a support comprising a metal oxide;
  (2) a binder comprising a colloidal metal oxide or colloidal metalloid oxide;
  (3) a first biocidal compound comprising silver nitrate; and
  (4) an acid;
(b) removing a sufficient amount of water to cross-link the binder with itself, the support, and/or the first biocidal compound to produce a first binder/biocidal composition; and
(c) contacting the first binder/biocidal composition produced in step (b) with a reducing agent comprising ascorbic acid to reduce at least some of the first biocidal compound to produce a first reduced biocidal/support composition.

106. The process of claim 105, wherein the metal oxide of the support is an adsorbent and/or catalyst compound.

107. The process of claim 105, further comprising oxidizing at least some of the first biocidal compound in the first reduced binder/biocidal composition to produce a first oxidized binder/biocidal composition.

108. The process of claim 105, wherein after step (c), admixing the first reduced binder/biocidal composition with a second biocidal compound to produce a second binder/biocidal composition.

109. The process of claim 108, further comprising contacting the second binder/biocidal composition with a reducing agent to reduce at least some of the second biocidal compound to produce a second reduced binder/biocidal composition.

110. The process of claim 109, further comprising oxidizing at least some of the second biocidal compound in the second reduced binder/biocidal composition.

111. The process of claim 106, wherein prior to step (a), the metal oxide of the support is (1) calcined at a particle temperature of from 200 to 700° C., and (2) contacted with a dilute acid, wherein the acid contacting is more than a surface wash but less than an etching, wherein the resultant acid treated metal oxide is not subsequently calcined.

112. The process of claim 111, wherein the metal oxide of the support is aluminum oxide.

113. The process of claim 105, wherein the support is aluminum oxide.

114. The process of claim 105, wherein the support is silicon dioxide.

115. The process of claim 105, wherein the support is an oxide of magnesium.

116. The process of claim 105, wherein after step (c), the first reduced biocidal/support composition is heated in air at from 80 to 1,500° C.

117. A process for producing a composition containing a biocidal compound comprising:
(a) admixing components comprising:
  (i) a binder comprising a colloidal metal oxide or colloidal metalloid oxide,
  (ii) a support comprising a metal oxide, and
  (iii) an acid,
  to produce a mixture,
(b) removing a sufficient amount of water from the mixture produced in step (a) to cross-link the binder with itself and/or the support to produce a binder/support system; and
(c) admixing the binder/support system produced in step (b) with a first biocidal compound comprising silver nitrate to produce a first binder/biocidal composition.

118. The process of claim 117, wherein the metal oxide of the support is an adsorbent and/or catalyst compound.

119. The process of claim 117, wherein after step (c), contacting the first binder/biocidal composition with a reducing agent comprising ascorbic acid to reduce at least some of the first biocidal compound to produce a reduced binder/biocidal composition.

120. The process of claim 119, further comprising oxidizing at least some of the first biocidal compound in the reduced binder/biocidal composition.

121. The process of claim 117, wherein prior to step (a), the metal oxide of the support is (1) calcined at a particle temperature of from 200 to 700° C., and (2) contacted with a dilute acid, wherein the acid contacting is more than a surface wash but less than an etching, wherein the resultant acid treated metal oxide is not subsequently calcined.

122. The process of claim 121, wherein the metal oxide of the support is aluminum oxide.

123. The process of claim 117, wherein the support is aluminum oxide.

124. The process of claim 117, wherein the support is silicon dioxide.

125. The process of claim 117, wherein the support is an oxide of magnesium.

126. A process for producing a composition containing an adsorbent and/or catalyst compound, comprising:
(a) admixing a support comprising a metal oxide with a first adsorbent and/or catalyst compound comprising silver nitrate to produce a mixture;
(b) heating the mixture produced in step (a) at from 80 to 1,800° C. to produce a heated mixture; and
(c) contacting the heated mixture produced in step (b) with a reducing agent comprising ascorbic acid to reduce at least some of the first adsorbent and/or catalyst compound to produce a first reduced adsorbent and/or catalyst/support composition.

127. A process for producing a composition containing an adsorbent and/or catalyst compound comprising:
(a) admixing a support comprising a metal-with a first adsorbent and/or catalyst compound comprising silver nitrate to produce a mixture;
(b) heating the mixture produced in step (a) at from 80 to 1,800° C. to produce a heated mixture;
(c) contacting the heated mixture produced in step (b) with a reducing agent comprising ascorbic acid to reduce at least some of the first adsorbent and/or catalyst compound to produce a reduced adsorbent and/or catalyst/support composition; and
(d) oxidizing at least some of the first adsorbent and/or catalyst compound in the reduced adsorbent and/or catalyst/support composition to produce an oxidized adsorbent and/or catalyst/support composition.

128. A process for producing a composition containing an adsorbent and/or catalyst compound, comprising:
(a) admixing a support comprising a metal oxide with an adsorbent and/or catalyst compound comprising silver nitrate to produce a mixture;

(b) drying the mixture to produce a dried mixture; and (c) contacting the dried mixture produced in step (b) with a reducing agent comprising ascorbic acid to reduce at least some of the adsorbent and/or catalyst compound to produce a reduced adsorbent and/or catalyst compound/support composition.

129. A process for producing a composition containing an adsorbent and/or catalyst compound comprising:

(a) admixing components comprising:
 (1) a support comprising a metal oxide;
 (2) a binder comprising a colloidal metal oxide or colloidal metalloid oxide;
 (3) a first adsorbent and/or catalyst compound comprising silver nitrate; and
 (4) an acid;

(b) removing a sufficient amount of water to cross-link the binder with itself, the support, and/or the adsorbent and/or catalyst compound to produce a first binder/adsorbent and/or catalyst composition; and (c) contacting the first binder/adsorbent and/or catalyst composition produced in step (b) with a reducing agent comprising ascorbic acid to reduce at least some of the first adsorbent and/or catalyst compound to produce a first reduced adsorbent and/or catalyst/support composition.

130. A process for producing a composition containing an adsorbent and/or catalyst compound comprising:

(a) admixing components comprising:
 (i) a binder comprising a colloidal metal oxide or colloidal metalloid oxide,
 (ii) a support comprising a metal oxide, and
 (iii) an acid,
 to produce a mixture, (b) removing a sufficient amount of water from the mixture produced in step (a) to cross-link the binder with itself and/or the support to produce a binder/support system; and (c) admixing the binder/support system produced in step (b) with a first adsorbent and/or catalyst compound comprising silver nitrate to produce a first binder/adsorbent and/or catalyst composition.

131. The composition produced by the process of claim 1.

132. The composition produced by the process of claim 24.

133. The composition produced by the process of claim 37.

134. The composition produced by the process of claim 40.

135. The composition produced by the process of claim 53.

136. The composition produced by the process of claim 61.

137. The composition produced by the process of claim 62.

138. The composition produced by the process of claim 63.

139. The composition produced by the process of claim 64.

140. The composition produced by the process of claim 65.

141. The composition produced by the process of claim 66.

142. The composition produced by the process of claim 89.

143. The composition produced by the process of claim 131.

144. The composition produced by the process of claim 105.

145. The composition produced by the process of claim 117.

146. The composition produced by the process of claim 126.

147. The composition produced by the process of claim 127.

148. The composition produced by the process of claim 128.

149. The composition produced by the process of claim 129.

150. The composition produced by the process of claim 130.

* * * * *